US012582685B2

(12) United States Patent
Bavington et al.

(10) Patent No.: US 12,582,685 B2
(45) Date of Patent: Mar. 24, 2026

(54) USES OF SACCHARIDES FROM PRASINOCOCCALES

(71) Applicant: Fjord Biotech AS, Sandnes (NO)

(72) Inventors: Charles Daniel Bavington, Tananger (NO); Benjamin Dahle, Tananger (NO); Lars Andreas Dahle, Tananger (NO); Svein Dahle, Tananger (NO); Claire Moss, Tananger (NO)

(73) Assignee: Fjord Biotech AS, Sandnes (NO)

( * ) Notice: Subject to any disclaimer, the term of this patent is extended or adjusted under 35 U.S.C. 154(b) by 364 days.

(21) Appl. No.: 18/018,835

(22) PCT Filed: Jul. 27, 2021

(86) PCT No.: PCT/EP2021/070984
§ 371 (c)(1),
(2) Date: Jan. 30, 2023

(87) PCT Pub. No.: WO2022/023331
PCT Pub. Date: Feb. 3, 2022

(65) Prior Publication Data
US 2023/0293609 A1 Sep. 21, 2023

(30) Foreign Application Priority Data
Jul. 31, 2020 (GB) ..................................... 2011973

(51) Int. Cl.
| | |
|---|---|
| A61K 36/02 | (2006.01) |
| A61K 31/192 | (2006.01) |
| A61K 36/05 | (2006.01) |
| A61K 47/02 | (2006.01) |
| A61K 47/10 | (2017.01) |
| A61K 47/22 | (2006.01) |
| A61L 15/40 | (2006.01) |
| A61P 17/00 | (2006.01) |
| A61P 31/12 | (2006.01) |

(52) U.S. Cl.
CPC ............ *A61K 36/05* (2013.01); *A61K 31/192* (2013.01); *A61K 47/02* (2013.01); *A61K 47/10* (2013.01); *A61K 47/22* (2013.01); *A61L 15/40* (2013.01); *A61P 17/00* (2018.01); *A61P 31/12* (2018.01)

(58) Field of Classification Search
CPC .................................................... A61K 9/1652
See application file for complete search history.

(56) References Cited

U.S. PATENT DOCUMENTS

| | | | |
|---|---|---|---|
| 10,383,891 B2 | 8/2019 | Klein | |
| 2015/0119355 A1* | 4/2015 | Bavington | ................ A61P 1/00 536/122 |

FOREIGN PATENT DOCUMENTS

| | | | |
|---|---|---|---|
| CN | 104147603 A | * | 11/2014 |
| TW | 201132345 A | * | 10/2011 |
| WO | WO-2006/003521 A1 | | 1/2006 |
| WO | WO-2013/167911 A1 | | 11/2013 |
| WO | WO-2018/104950 A1 | | 6/2018 |

OTHER PUBLICATIONS

Ahmadi Azin et al: "Antiviral Potential of Algae Polysaccharides Isolated from Marine Sources: A Review", Biomed Research International, vol. 2015, Jan. 1, 2015 (Jan. 1, 2015), pp. 1-10, XP055890924, ISSN: 2314-6133, DOI: 10.1155/2015/825203 Retrieved from the Internet: URL:http://downloads.hindawi.com/journals/bmri/2015/825203.pdf> p. 3, last paragraph, p. 7, last paragraph.
Fabregas J. et al: "In vitro inhibition of the replication of haemorrhagic septicaemia virus (VHSV) and African swine fever virus (ASFV) by extracts from marine microalgae", Antiviral Research, vol. 44, No. 1, Nov. 1, 1999 (Nov. 1, 1999), pp. 67-73, XP055891140, NL ISSN: 0166-3542, DOI: 10.1016/S0166-3542(99)00049-2. Retrieved from the Internet: URL:https://www.sciencedirect.com/science/article/pii/S0166354299000492/pdfft?md5=6a2b0520ff9a5692fld2a7895a74515f&pid=1-s2.0-S0166354299000492-main.
International Search Report and Written Opinion on PCT App. PCT/EP2021/070984 dated Feb. 25, 2022 (18 pages).
Yegappan Ramanathan et al: "Carrageenan based hydrogels for drug delivery, tissue engineering and wound healing", Carbohydrate Polymers, Applied Science Publishers, Ltd Barking, GB, vol. 198, Jun. 23, 2018 (Jun. 23, 2018), pp. 385-400, XP085437672, ISSN: 0144-8617, DOI: 10.1016/J.CARBPOL.2018.06.086, p. 392-p. 393.

* cited by examiner

*Primary Examiner* — Qiuwen Mi
(74) *Attorney, Agent, or Firm* — Foley & Lardner LLP

(57) ABSTRACT

The present invention relates to a sulphated heteropolymer polysaccharide obtainable from the order of Prasinococcales polysaccharide wherein the average molecular weight of the polysaccharide is between 1,000 and 40,000 kDa, or a fragment of for use in the treatment of skin irritation, wound repair, fibrotic conditions, keloid trait scarring or keloid scars, viral infection, as a biological carrier or scaffold or bio-lubricant; methods of preparing the same and uses thereof, such as in antiviral compositions.

20 Claims, 10 Drawing Sheets

Figure 7
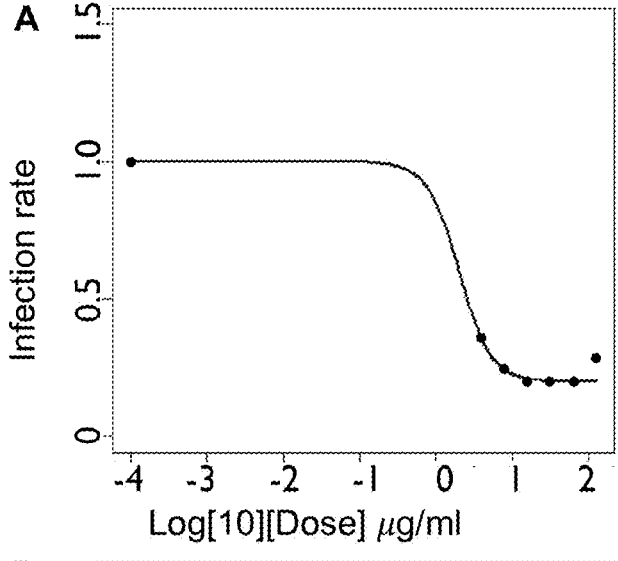
| RSV infection rate (normalised against control) | |
|---|---|
| Sample | *Filtered high MW polysaccharide* |
| EC50 | 2.02 µg/ml |
| Error | 0.00767 |
| Selectivity index | 250 |
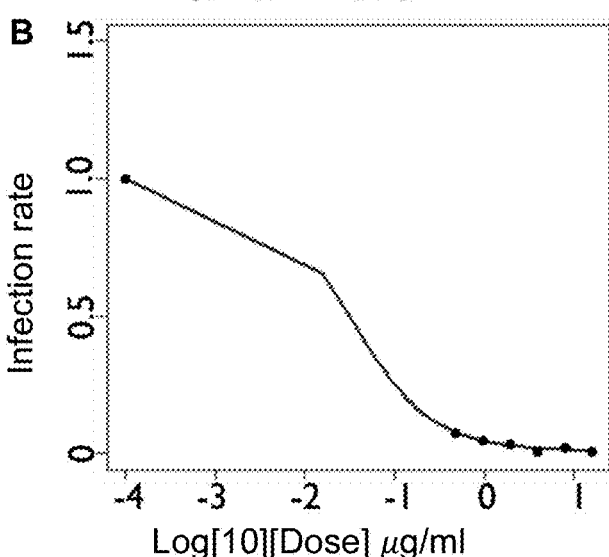
| RSV infection rate (normalised against control) | |
|---|---|
| Sample | *Depolymerised saccharide 1* |
| EC50 | 0.03 µg/ml |
| Error | 0.00015 |
| Selectivity index | >5000 |
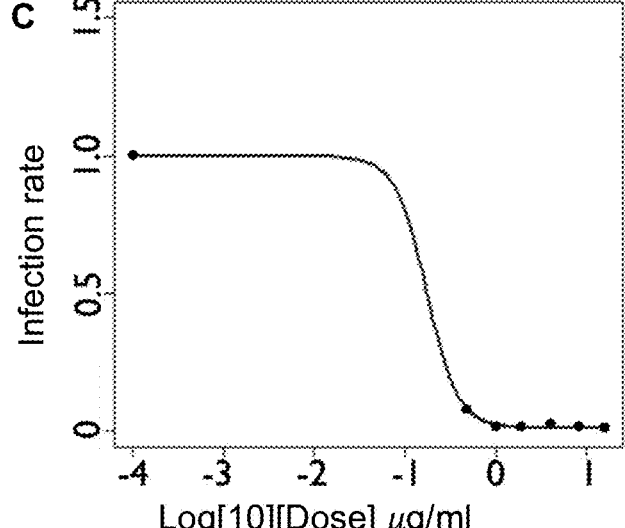
| RSV infection rate (normalised against control) | |
|---|---|
| Sample | *Depolymerised saccharide 2* |
| EC50 | 0.17 µg/ml |
| Error | 0.00031 |
| Selectivity index | >5000 |

Figure 8
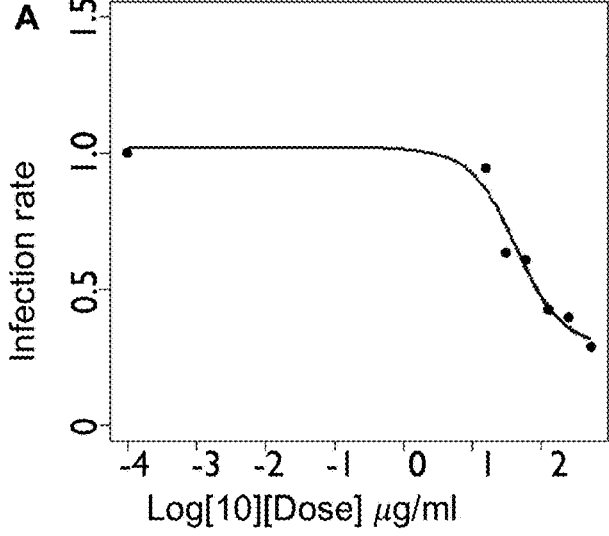
| HSV infection rate (normalised against control) | |
|---|---|
| Sample | *Filtered high MW polysaccharide* |
| EC50 | 43.87 μg/ml |
| Error | 0.01906 |
| Selectivity index | >11 |
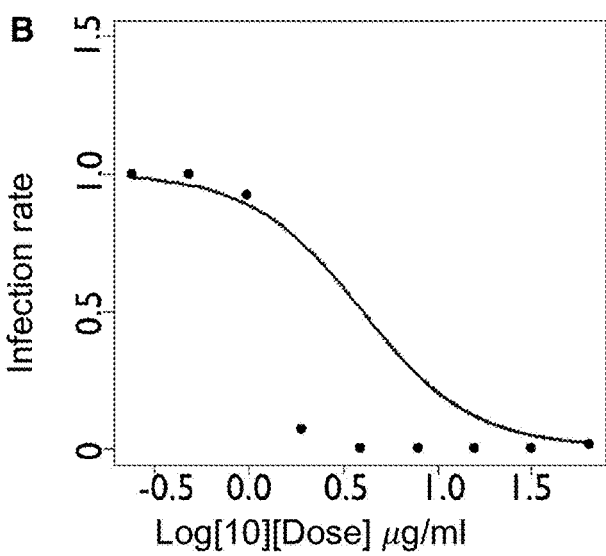
| HSV infection rate (normalised against control) | |
|---|---|
| Sample | *Depolymerised saccharide 1* |
| EC50 | 3.99 μg/ml |
| Error | 0.80134 |
| Selectivity index | >380 |
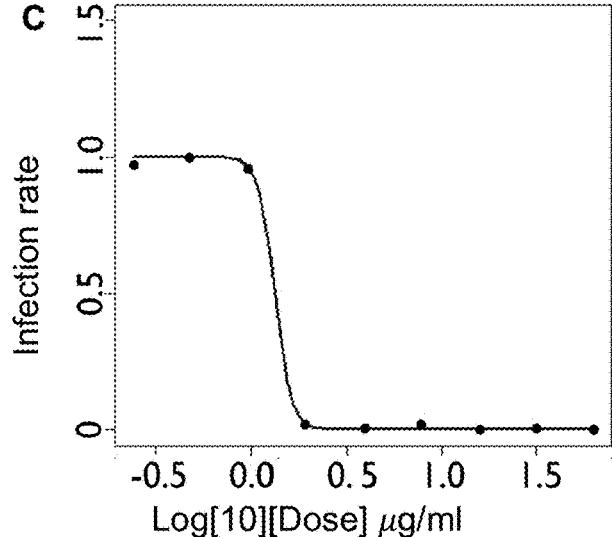
| HSV infection rate (normalised against control) | |
|---|---|
| Sample | *Depolymerised saccharide 2* |
| EC50 | 1.33 μg/ml |
| Error | 0.00171 |
| Selectivity index | >380 |

Figure 9

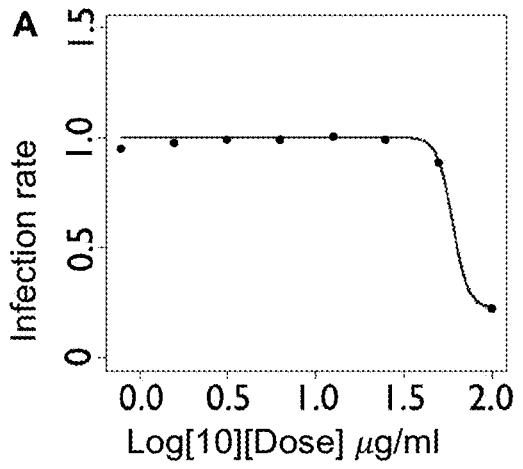

A

| EV68 infection rate (normalised) | |
|---|---|
| Sample | *Filtered high MW polysaccharide* |
| EC50 | 60.15 $\mu$g/ml |
| Error | 0.00348 |
| Selectivity index | <10 |

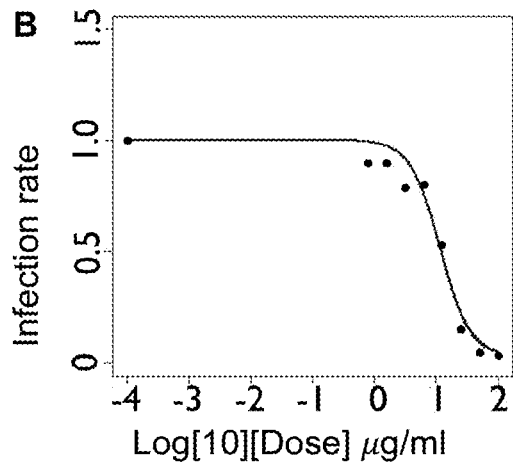

B

| EV68 infection rate (normalised) | |
|---|---|
| Sample | *Autoclaved high MW polysaccharide* |
| EC50 | 11.63 $\mu$g/ml |
| Error | 0.04489 |
| Selectivity index | >45 |

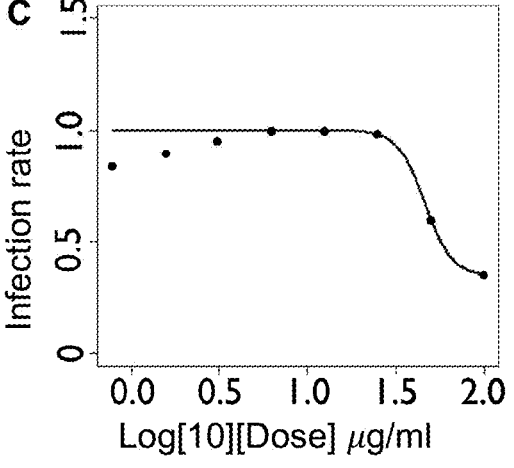

C

| EV68 infection rate (normalised) | |
|---|---|
| Sample | *Depolymerised saccharide 1* |
| EC50 | 46.4 $\mu$g/ml |
| Error | 0.03981 |
| Selectivity index | >10 |

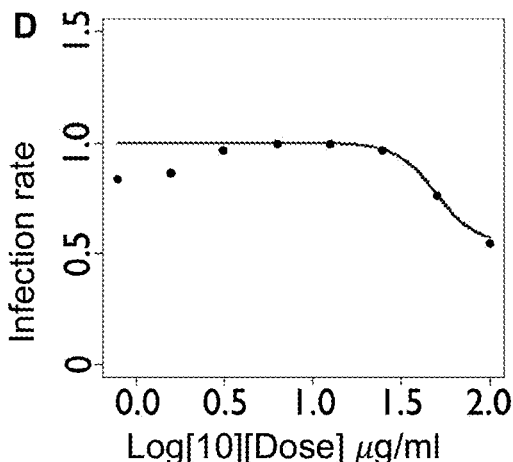

D

| EV68 infection rate (normalised) | |
|---|---|
| Sample | *Depolymerised saccharide 2* |
| EC50 | 49.93 $\mu$g/ml |
| Error | 0.04714 |
| Selectivity index | >10 |

Figure 10
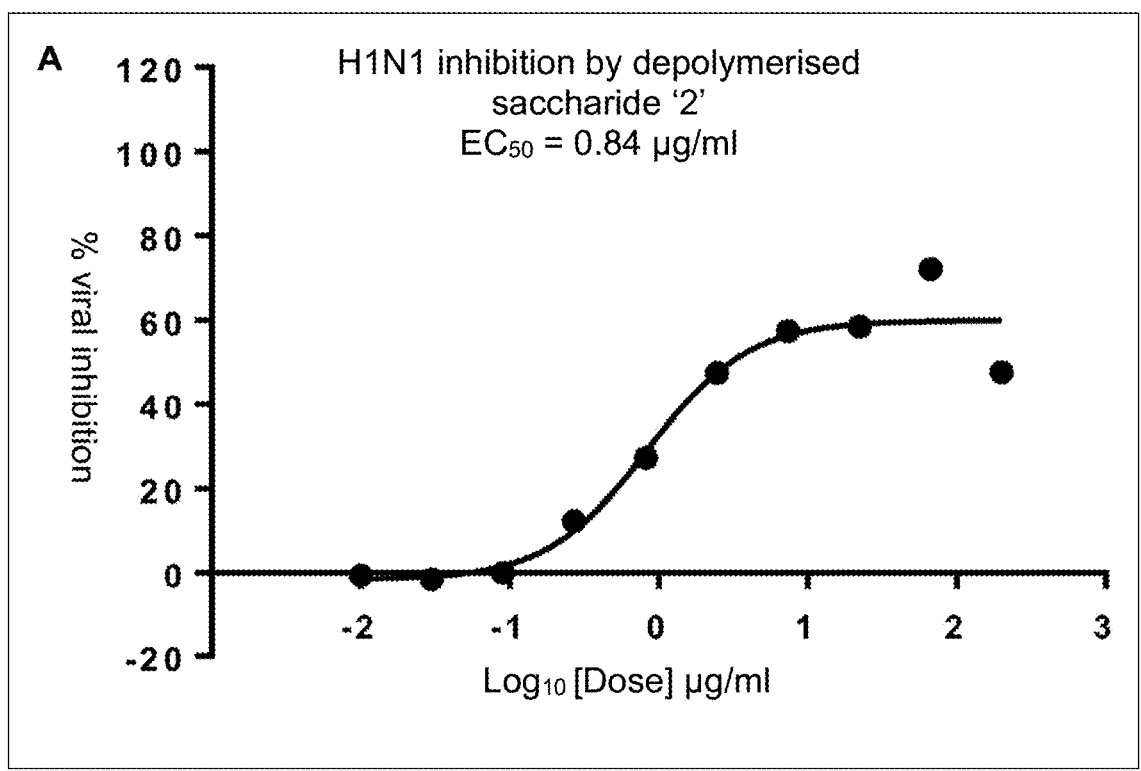
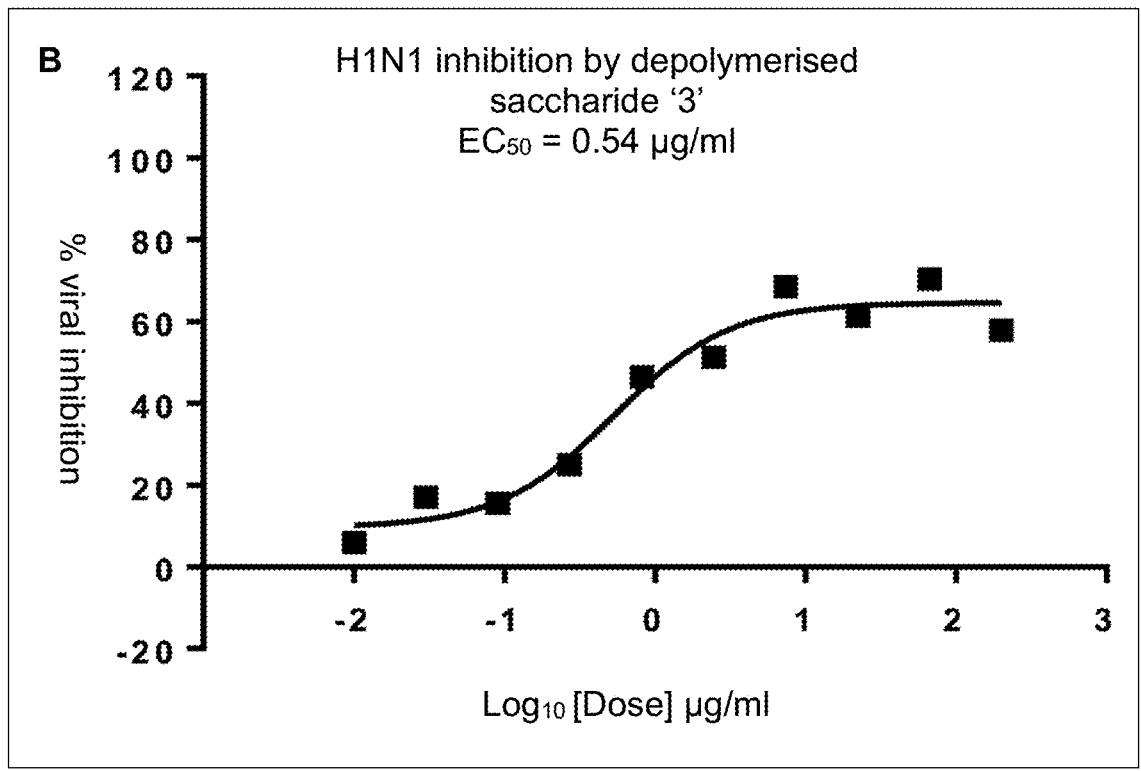

USES OF SACCHARIDES FROM PRASINOCOCCALES

CROSS-REFERENCE TO RELATED APPLICATIONS

This application claims the benefit of priority to International Application No. PCT/EP2021/070984, filed on Jul. 27, 2021, which claims the benefit of and priority to Great Britain Patent Application No. 2011973.1, filed Jul. 31, 2020, both of which are hereby incorporated by reference in their entireties.

FIELD OF THE INVENTION

The invention relates to a polysaccharide or a fragment of a polysaccharide obtainable from the microalga, *Prasinococcus capsulatus* and strains related to *P. capsulatus*. Further, it relates to compositions comprising a polysaccharide or a fragment of a polysaccharide obtainable from the microalgae, *Prasinococcus capsulatus* or an algal strain related to *P. capsulatus* and prophylactic and/or therapeutic uses of said compositions.

BACKGROUND OF THE INVENTION

Patent document EP2846813B1 describes the composition of a polysaccharide and derivatives of the polysaccharide, obtainable from the microalgae *Prasinococcus capsulatus* and strains related to *P. capsulatus*. EP2846813B1 also discloses the effects of these compositions on inflammatory responses of human cells, and on immune system disorders.

The current invention describes new uses of the previously disclosed compositions in EP2846813B1, as active agents to protect skin from irritants, as topical treatments to promote wound healing and prevent scar formation and fibrosis, as topical anti-viral agents, as medical lubricants, and for encapsulation technologies and tissue engineering.

*Prasinococcus capsulatus*, a relatively recently discovered species has been shown to produce polysaccharides (Miyashita, et al. 1993. *Prasinococcus capsulatus Gen. Et Sp. Nov., A New Marine Coccoid Prasinophyte*. J. Gen. Appl. Microbiol., 39, 571-582; Miyashita, et al. 1995. *Composition and nature of extracellular polysaccharide produced by the type strain of a newly isolated coccoid prasinophyte, Prasinococcus capsulatus*. J. Marine Biotechnol., 3, 136-139).The polysaccharide and fragments of the polysaccharide, obtainable from the microalgae *Prasinococcus capsulatus* and strains related to *P. capsulatus*, as previously disclosed in EP2846813B1, has a unique sulphated saccharide composition.

SUMMARY OF THE INVENTION

This invention describes new uses of the previously disclosed polysaccharide, and fragments of the polysaccharide, obtainable from *Prasinococcus capsulatus* or an algal strain related to *P. capsulatus*, as described in EP2846813B1. More particularly, the present invention describes compositions comprising said polysaccharides as active agents to protect skin from irritants, as topical treatments to promote wound healing and prevent scar formation and fibrosis, as anti-viral agents, as medical lubricants, and for encapsulation technologies and tissue engineering.

Accordingly, a first aspect of the present invention provides a polysaccharide wherein the average molecular weight of the polysaccharide is between 1,000 and 40,000 kDa, or a fragment of polysaccharide wherein the average molecular weight of the fragment of the polysaccharide is between 5 and <1000 kDa, wherein the polysaccharide is a sulphated heteropolymer obtainable from the order of Prasinococcales, for use in the treatment of skin irritation, wound repair, fibrotic conditions, keloid trait scarring or keloid scars, viral infection, as a biological carrier or scaffold or bio-lubricant.

Suitably a strain related to *Prasinococcus capsulatus* may include a strain of the order Prasinococcales. In embodiments the polysaccharide can be a polysaccharide associated with the cell wall of the microalgae, and/or be present in a homogenate of the microalgae, and/or secreted polysaccharide or exopolysaccharide. The polysaccharide may be provided in an isolated, purified, or semi-purified form. In embodiments the polysaccharides can be a purified material that has been separated from cell biomass, such that the polysaccharide is at least 50% polysaccharide by weight, and more preferably above 75% polysaccharide by weight, more preferably above 80% by weight, more preferably about 95% by weight.

A polysaccharide or fragment thereof according to the present invention can comprise about:

20 to 30% Glucose
30 to 60% Galactose
4 to 19% Arabinose
2 to 6% Uronic acids
and a small percentage (1 to 10%) of other sugars, more particularly
Rhamnose
Xylose
Mannose
(% by weight).

Suitably, a polysaccharide or fragment thereof according to the present invention can have a sulphate content of about 17 to 35% by weight, suitably, 20 to 30% by weight, suitably the polysaccharide may have a sulphate content of about 25% by weight (as a percentage of molecular weight of the molecule).

Suitably, fragments of the invention can be depolymerised polysaccharides prepared by any known method, suitably a free radical or photochemical method or by physical processes or by hydrolysis.

Suitably, a polysaccharide or fragment thereof according to the present invention constitutes greater than 80% (by mass) of the dried product.

Suitably, the polysaccharide may have an average molecular weight of between 5,000 and 20,000 kDa or a fragment of the polysaccharide may have an average molecular weight between 20 and 500 kDa.

According to a second aspect of the present invention, there is provided a composition comprising a polysaccharide or fragment thereof according to the first aspect of the invention, an aqueous solution and, optionally, wherein the aqueous solution comprises a balanced salt solution and/or a preservative, for use in the treatment of skin irritation, wound repair, fibrotic conditions, keloid trait scars, viral infection, as a biological scaffold, or bio-lubricant. Suitably the composition may be a topical composition for application to the surface of skin or to the nasal, vaginal, or rectal surfaces.

Suitably, the composition may be a topical composition for application to the surface of wounds, and/or as a topical anti-viral agent.

In embodiments the polysaccharide, or fragment thereof is provided in an amount between 0.001% to 2%, optionally between 0.01% and 2% by weight (w/v) of the composition, optionally, between 0.1 and 1.5%, by weight (w/v) of the composition.

Suitably, the polysaccharide, or the fragment thereof or the composition may be a topical administration provided by a gel, cream, or ointment.

According to a third aspect of the present invention there is provided a composition according to the second aspect of the invention for use in the treatment of skin irritation. Suitably, a composition according to the second aspect that further comprises at least one anti-oxidant, optionally wherein the antioxidant is a tocopherol or mixture of tocopherols, for example, tocopherol acetate in an amount between 0.1 and 2.5% by weight (w/v), or astaxanthin in an amount between 0.005 and 0.1% by weight (w/v), is provided for use in the treatment of skin irritation.

According to a fourth aspect of the present invention, there is provided a composition according to the second aspect of the invention for use in the treatment of wounds. Suitably there is provided a composition according to the second aspect of the invention and further comprising an antiseptic, for example, chlorhexidine in an amount between 0.01 and 10% by weight (w/v), and/or an analgesic, for example, ibuprofen in an amount between 1 and 5% by weight (w/v), and/or vitamins, for example, vitamin E, a tocopherol or mixed tocopherols between 0.1 to 2.5% by weight (w/v), for use in the treatment of wounds.

According to a fifth aspect of the present invention, there is provided a wound dressing material comprising polysaccharide or a fragment thereof as discussed in the first aspect of the invention or a composition of the second aspect of the invention, optionally wherein the material comprises fibers or films of the polysaccharide.

In embodiments of the fifth aspect of the invention, the composition may further comprise a silver sulfadiazine in an amount between 0.05 and 0.25% by weight (w/v).

According to a sixth aspect of the present invention, there is provided a method for preparing the material according to the fifth aspect, wherein the material comprises fibres of the polysaccharide and the method comprises the steps of:

preparing an aqueous solution of between 0.01 and 2% by weight (w/v) of polysaccharide having an average molecular weight between 1,000 and 40,000 kDa or a fragment thereof; and forming the polysaccharide fibres by wet spinning the solution into a bath of solvent comprising between 70 to 100% ethanol, methanol or acetone.

According to a seventh aspect of the present invention, there is provided a method for preparing the material according to the fifth aspect, wherein the material comprises films of the polysaccharide and the method comprises the steps of:

preparing an aqueous solution of between 0.01 and 2% by weight (w/v) of polysaccharide having an average molecular weight between 1,000 and 40,000 kDa or a fragment thereof;

mixing the aqueous solution with a plasticizing agent;

heating the mixture to a temperature of between 30° C. and 90° C.; and casting the solution to a thin sheets, optionally of between 2 and 5 mm, by wet or solvent casting, and drying the thin sheets to form the polysaccharide films.

Suitably the plasticizing agent may be a polyol solution, for example, a glycerol solution, at 0.05 to 2% by weight (w/v) or, optionally, at 0.25 and 1% by weight (w/v).

According to an eighth aspect of the present invention, there is provided an anti-viral composition comprising a polysaccharide or a fragment thereof according to the first aspect of the invention. Suitably, the anti-viral composition may be effective against one or more members of the viral families Orthomyxoviridae, Picornaviridae, Herpesviridae and Paramyxoviridae. For example, of the group consisting of: a H1N1 influenza virus, Rhinovirus virus EV-D68, Herpes simplex virus 1 (HSV1) and respiratory syncytical virus.

Suitably, the antiviral composition may also be effective against one or more members of the viral families consisting of: Adenoviridae, Papovaviridae, Retroviridae, Flaviviridea, Hepadnaviridae, Poxviridae and Coronaviridae such as the virus Sars CoV-2.

Suitably, the anti-viral composition may comprise an aqueous solution, optionally, wherein the aqueous solution may comprise a balanced salt solution and/or a preservative for use in the treatment of viral infection.

Suitably, the polysaccharide, or fragment thereof may be provided in an amount between 0.0001 and 1% by weight (w/v) of the composition, optionally, between 0.001 and 0.1%, by weight (w/v) of the composition.

Suitably, the polysaccharide fragment may have an average molecular weight in the range of 20 to 50 kDa or approximately 35 KDa.

According to a ninth aspect of the present invention, there is provided an antiviral spray comprising a polysaccharide or a fragment thereof according to the first aspect of the invention or a composition of the eighth aspect of the invention, comprising a powder for delivery to a mucosal surface. Advantageously, powder based antiviral sprays provide good formulation stability and easy administration. As such, it can be an advantageous means for administering high doses of the polysaccharide or fragment thereof according to the first aspect or an anti-viral composition of the eighth aspect.

Suitably, in embodiments of the ninth aspect the powder is a dry powder. Suitably, a dry powder comprises less than 10% moisture, optionally less than 4% moisture, optionally less than 3% moisture, optionally less than 2% moisture, and optionally less than 1% moisture.

According to a tenth aspect of the present invention there, is provided an anti-viral spray comprising a polysaccharide or fragment thereof according to the first aspect of the invention or a composition of the eighth aspect of the invention, and at least one ionic or non-ionic osmolarity adjusting agent to form a hyperosmolar aqueous formulation. Suitably, this spray may be used for nasal delivery.

Suitably in embodiments of the tenth aspect of the invention, the osmolarity adjusting agents is/are selected from one or more of a metal halide salt, suitably sodium or potassium chloride or a mixture thereof, at a concentration of between 0.1 and 3% by weight (w/v), a mono-, di- or oligosaccharide between 200 and 10,000 Da, and/or a low molecular weight polyol, preferably glycerol, mannitol or sorbitol, at a concentration of between 1 and 15% by weight (w/v).

According to an eleventh aspect of the present invention, there is provided a bio-lubricant comprising a polysaccharide or fragment thereof as set out in the first aspect of the invention or a composition of the second aspect of the invention and further comprising between 1 and 15% by weight, preferably 5 to 10% by weight (w/v), of a humectant polyol.

Suitably the bio-lubricant may comprise a humectant polyol selected from a sugar alcohol or glycerol, suitably glycerol.

According to a twelfth aspect of the present invention, there is provided a method of lubricating comprising a) providing a bio-lubricant of the eleventh aspect of the invention to mucosal tissue, or b) providing a bio-lubricant of the eleventh aspect of the invention to a medical instrument, or c) providing a bio-lubricant of the eleventh aspect of the invention to a condom.

According to a thirteenth aspect of the present invention, there is provided a use of a polysaccharide or a fragment thereof or a composition as discussed in the first or second aspect of the present invention in the preparation of a carrier device, optionally wherein the carrier device can be a microparticle or hydrogel or scaffold, or 3D printed scaffold, for the protection, delivery and controlled release of biological substances, or for the protection, growth support or delivery of live cells.

Suitably the use of the thirteenth aspect of the invention may comprise complexing a solution of the polysaccharide with another polyelectrolyte to form a microparticle.

Suitably the use of the thirteenth aspect of the invention may comprise the steps of: providing the polysaccharide solution between 0.1 to 2% by weight (w/v); and extruding the polysaccharide solution from a tip of a capillary tube, or narrow gauge needle, into a solution of poly(diallyldimethylammonium chloride) between 1 and 20% by weight, and having a molecular weight between 1 and 500 kDa.

Suitably the use of the thirteenth aspect of the invention may further comprise the step of encapsulating an active pharmaceutical ingredient into the microparticle by pre-mixing with the polysaccharide solution. Suitably such encapsulation may comprise any methods as known in the art, for example polyelectrolyte methods.

Suitably, the use of the thirteenth aspect of the invention may comprise encapsulation of the active ingredient into microparticles by pre-mixing with the polysaccharide solution and spray drying, optionally, comprising the step of providing a spray drying apparatus having an inlet temperature between 180 to 200° C., an outlet temperature between 80 to 100° C., and a flow rate of 25 to 40 ml/min.

Suitably the use of the thirteenth aspect of the invention may further comprise encapsulating a mammalian or bacterial cell into the microparticle by pre-mixing with the polysaccharide.

Optionally, the carrier device is prepared using three-dimensional printing process. Suitably further structural and/or functional components may be provided in the scaffold, for example collagen.

According to a fourteenth aspect of the present invention there is provided a carrier device as prepared according to the thirteenth aspect of the invention, wherein the carrier device comprises a polyelectrolyte complexing solution of the polysaccharide to form a microparticle.

Suitably a polysaccharide or fragment as discussed herein can be provided as part of a composition for use in:

the protection of skin against environmental, chemical and biological irritants, the topical treatment and management of all types of wounds to promote wound healing, including the reduction of scaring, the treatment and prevention of fibrotic conditions, including the treatment of post-surgical adhesions and fibrous growths, and conditions such as keloid trait, which share similar biology with fibrous adhesions, anti-viral therapy and prophylaxis, including nasal anti-viral sprays, topical applications and other applications, a medical lubricant, for example for intravaginal application to promote female reproductive health, and/or carrier devices for molecules or cells, in the form of particles, capsules, hydrogels and scaffolds, which can be used for drug delivery, tissue engineering and regenerative medicine applications.

Such a composition may be suitable for topical administration. In embodiments the composition can be either for topical application to the skin, nasal, vaginal or rectal mucosa, or topical application to wounds including surgical wounds.

Compositions for topical administration may be provided, for example, as a gel, cream or ointment. Such compositions can be applied directly to the affected surface or carried on a suitable support, such as a bandage, gauze, mesh or the like that can be applied to an area to be treated.

A polysaccharide or fragment may be provided as a pharmaceutically acceptable salt or pharmaceutically acceptable solvate. Suitably a polysaccharide or fragment may be provided as a salt or solvate suitable for its use, for example to retain the polysaccharide in a form suitable for its physical use or for example to stabilise or preserve the polysaccharide. In embodiments the polysaccharide or fragment or derivative can be administered alone, or in admixture with a pharmaceutical carrier, excipient or diluent selected with regard to the intended route of administration and standard pharmaceutical practice. A pharmaceutical carrier can be a physiologically acceptable carrier, either organic or inorganic, natural or synthetic with which the polysaccharide or oligosaccharide thereof of the present invention can be combined to facilitate the application.

In embodiments a polysaccharide or fragment can be admixed with any suitable binder (s), suspending agent (s), coating agent (s), solubilising agent (s), carrier(s), preservative(s), or buffer stabiliser(s).

A composition of the invention may also contain one or more further active compounds selected as necessary for the condition being treated. For example, a composition may comprise a further active compound which targets distinct pathways or mechanisms from that targeted by the product of the invention. This may provide improved efficacy, for example a synergistic effect.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness. Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

In one embodiment, throughout the patent application as filed a powder could be a dry powder. By the term "dry powder" it is meant a powder having a moisture content of less than 10%.

BRIEF DESCRIPTION OF THE FIGURES

The accompanying drawings illustrate presently exemplary embodiments of the disclosure, and together with the general description given above and the detailed description of the embodiments given below, serve to explain, by way of example, the principles of the disclosure.

FIG. 7 illustrates the effects of the polysaccharides and fragments of the polysaccharide on the infectivity of respiratory syncytial virus in Hep2 cells wherein: (A) provides activity data plotted against the log [10] of high molecular weight (MW) polysaccharide test concentrations: (B) provides activity data plotted against the log [10] of saccharide fragment '2' test concentrations. The plots illustrate the calculation of the EC50 values for the test saccharides.

FIG. 8 illustrates the effects of the polysaccharide and fragments of the polysaccharide on the infectivity of herpes simplex virus-1 in MRCS cells wherein; (A) provides activity data plotted against the log[10] of high molecular weight (MW) polysaccharide test concentrations; (B) provides activity data plotted against the log[10] of saccharide fragment '1' test concentrations; (C) provides activity data plotted against the log[10] of saccharide fragment '2' test concentrations. The plots illustrate the calculation of the EC50 values for the test saccharides.

FIG. 9 illustrates the effects of the polysaccharide and fragments of the polysaccharide on the infectivity of rhinovirus/EV-D68 in MRC5 cells wherein; (A) provides activity data plotted against the log[10] of high molecular weight (MW) polysaccharide test concentrations; (B) provides activity data plotted against the log[10] of saccharide fragment '1' test concentrations; (C) provides activity data plotted against the log[10] of saccharide fragment '2' test concentrations. The plots illustrate the calculation of the EC50 values for the test saccharides.

FIG. 10 illustrates the effects of fragments of the polysaccharide on the infectivity of influenza H1 N1 in A549 cells wherein; (A) provides activity data plotted against the log[10] of saccharide fragment '2' test concentrations; (B) provides activity data plotted against the log[10] of saccharide fragment '3' test concentrations. The plots illustrate the calculation of the EC50 values for the anti-viral activity of test saccharides.

DETAILED DESCRIPTION

Figure 1A:
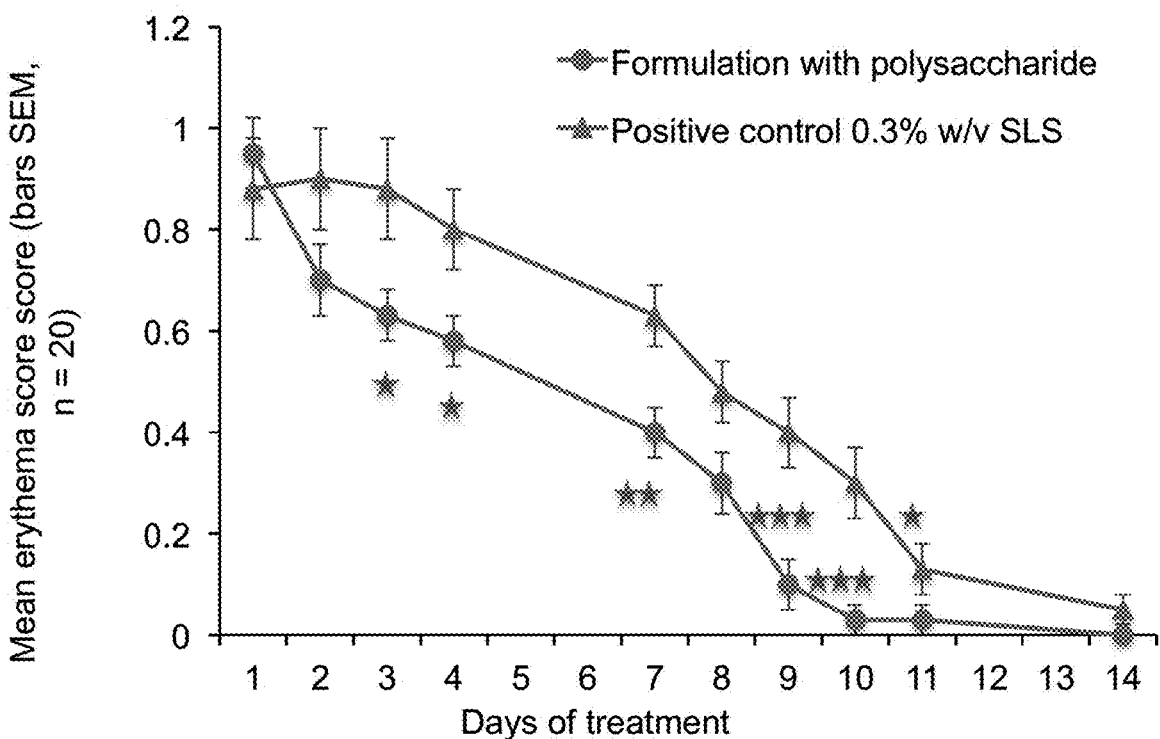
FIGS. 1A and 1B illustrates the reduction in SLS-induced erythema (measured by erythema scoring) of compositions containing the polysaccharide (A), or fragments of the polysaccharide (B), wherein there is provided example data of the effects of *P. capsulatus* polysaccharide and polysaccharide fragments on erythema score compared to the positive control (0.3% w/v SLS). After application the test article produced statistically significant anti-inflammatory effects on the skin (P<0.05) when compared to the untreated site between, and including, the day 4 and day 11 time points (error bars=SEM, n=20, asterisks indicate statistical significance).
Figure 1B:
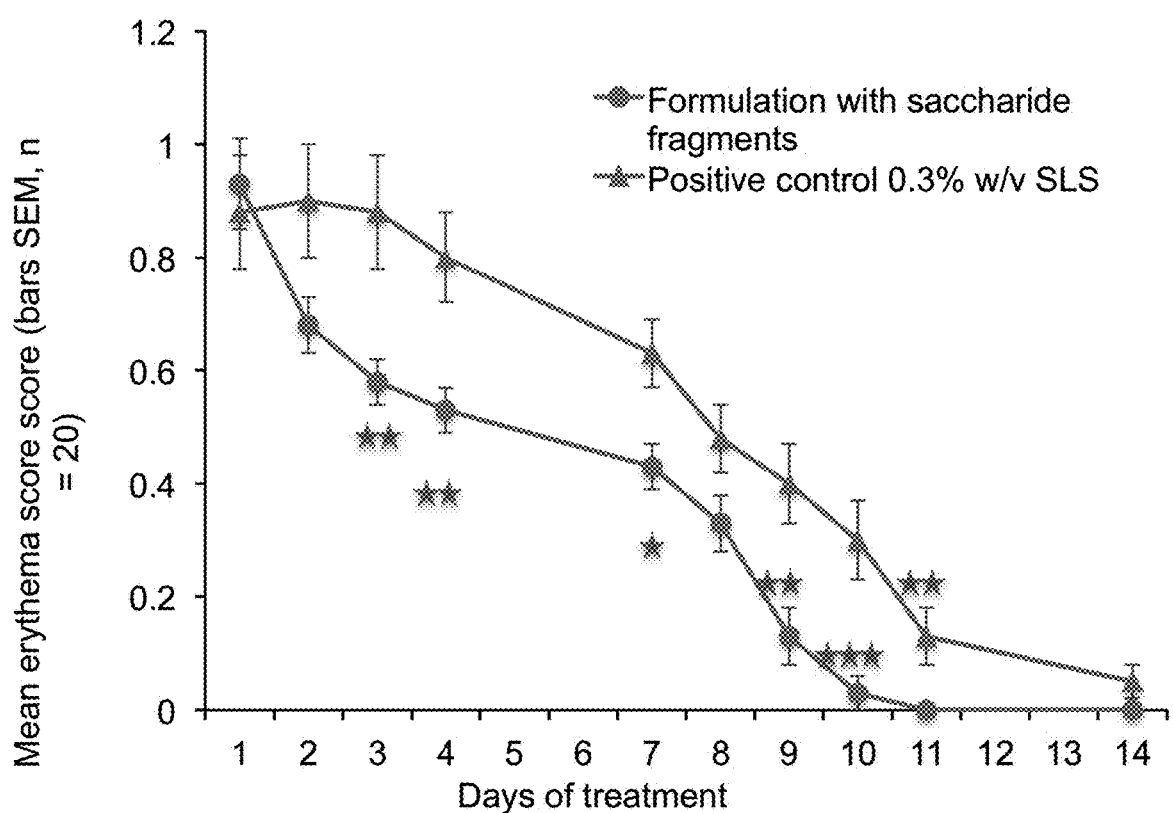
Figure 2:
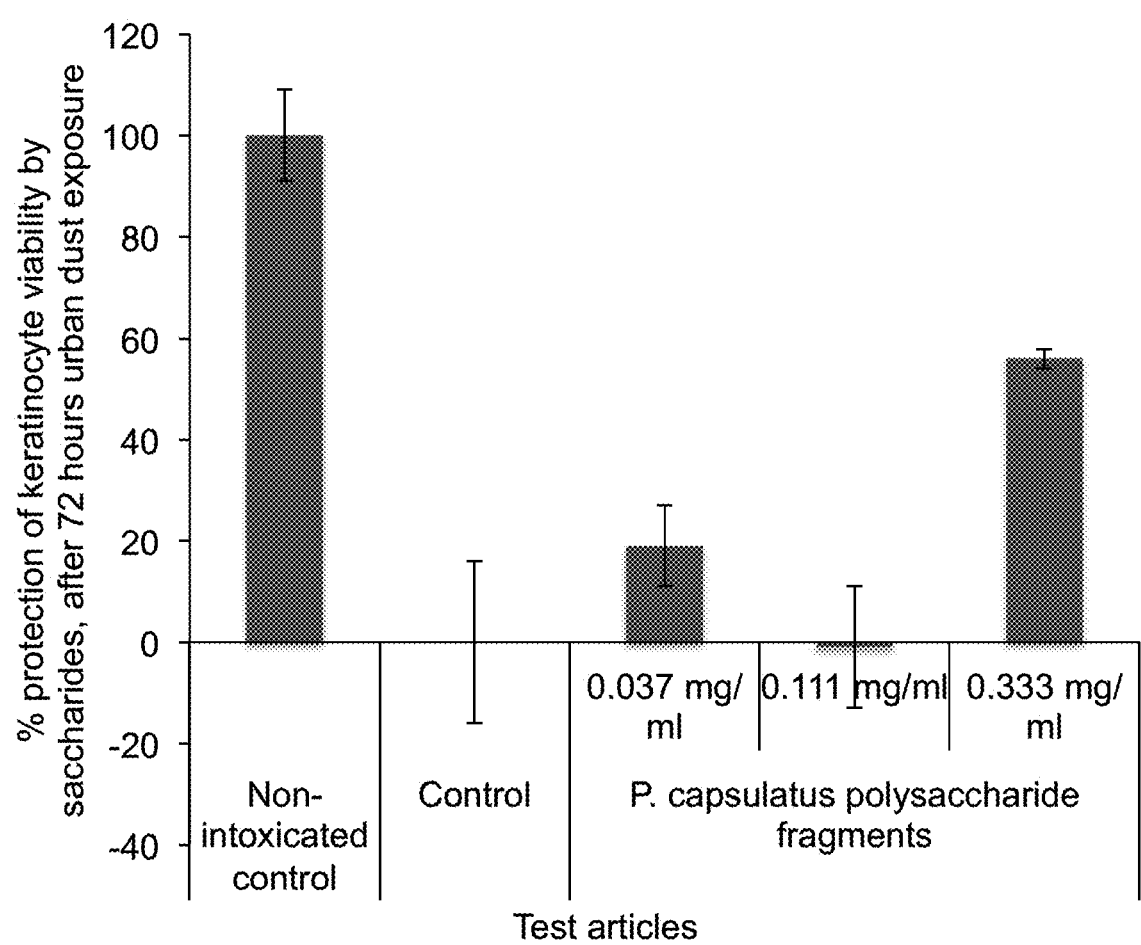
FIG. 2 illustrates the % protection provided by fragments of the polysaccharide on keratinocyte viability, under urban dust intoxication conditions, wherein there is provided example data of the protection effects of fragments of the polysaccharide, after 72 hours incubation in vitro compared to treated (control with urban dust) and untreated (non-intoxicated) controls (error bars=standard deviation).
Figure 3A:
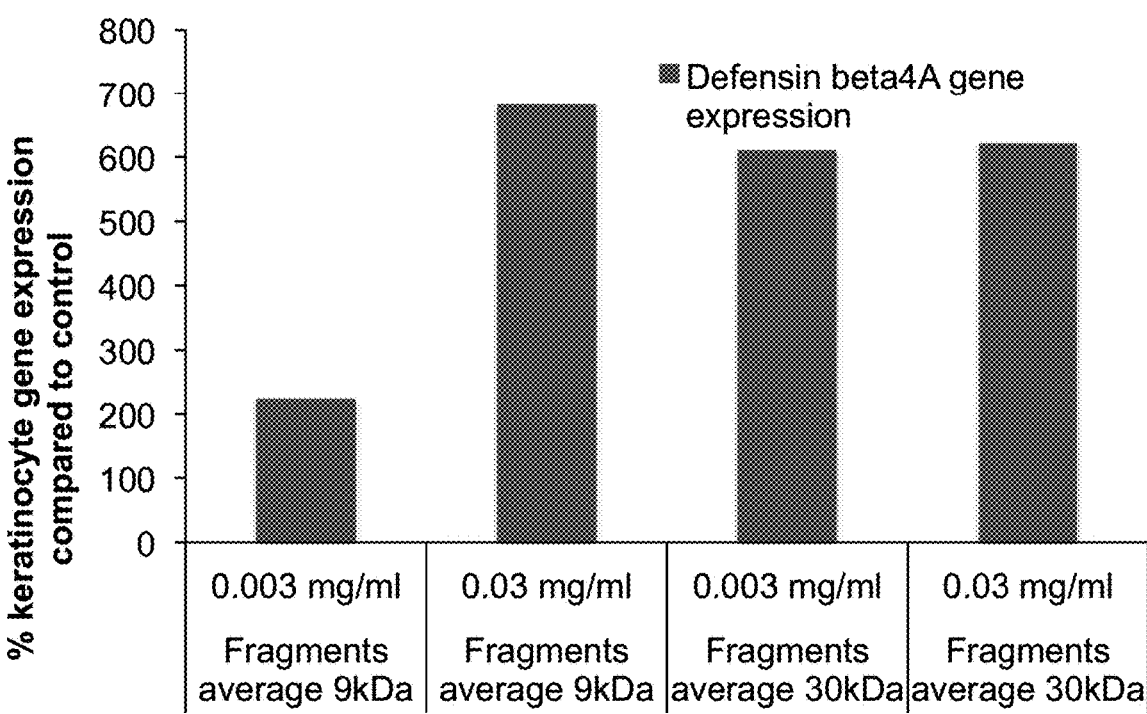
FIGS. 3A and 3B illustrates the effects of fragments of the polysaccharide on the gene expression of keratinocytes under basal conditions, wherein there is provided example data of the effects of fragments or derivatives of the polysaccharide on gene expression of the anti-microbial marker DEFB4A (A) and epidermal differentiation marker KRT10 (B). Treatment with the fragments results in a dose dependent enhancement of the expression of these genes under the conditions test % relative gene expression is calculated with the formula $(\frac{1}{2}^{number\ of\ cycles}) \times 10^6$, where the reference gene GAPDH was used for data normalisation.
Figure 3B:
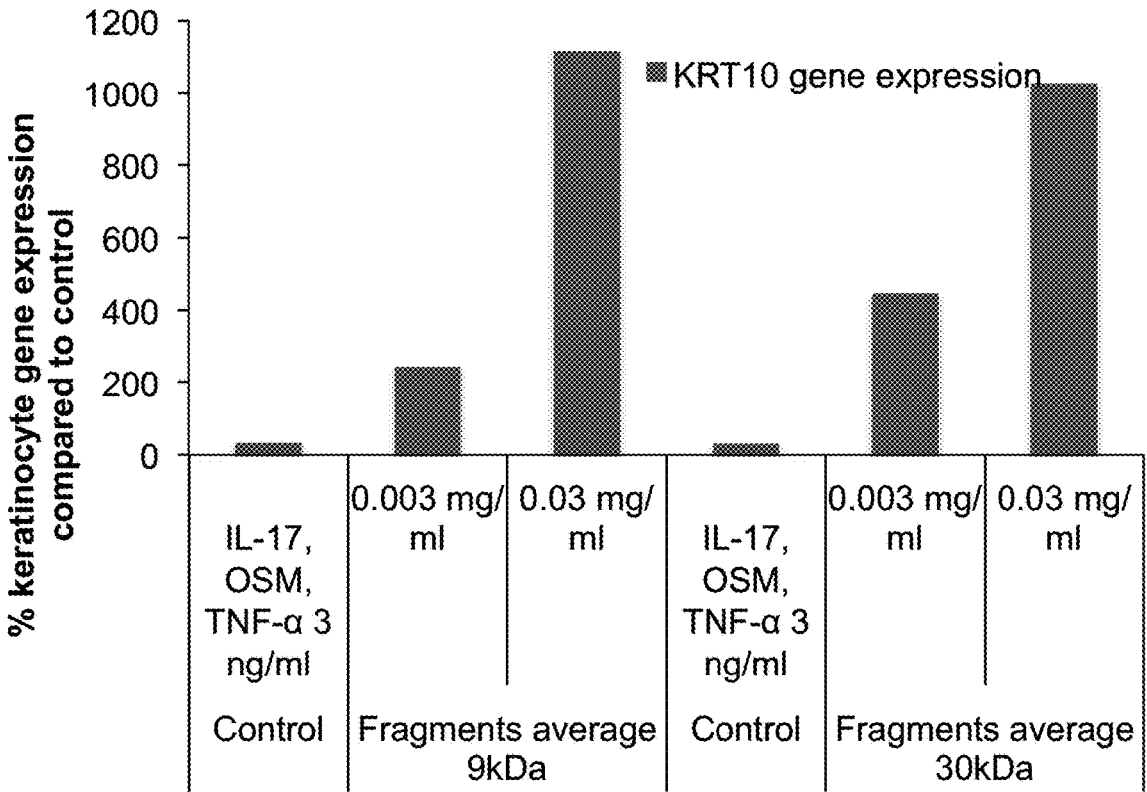
Figure 4A:
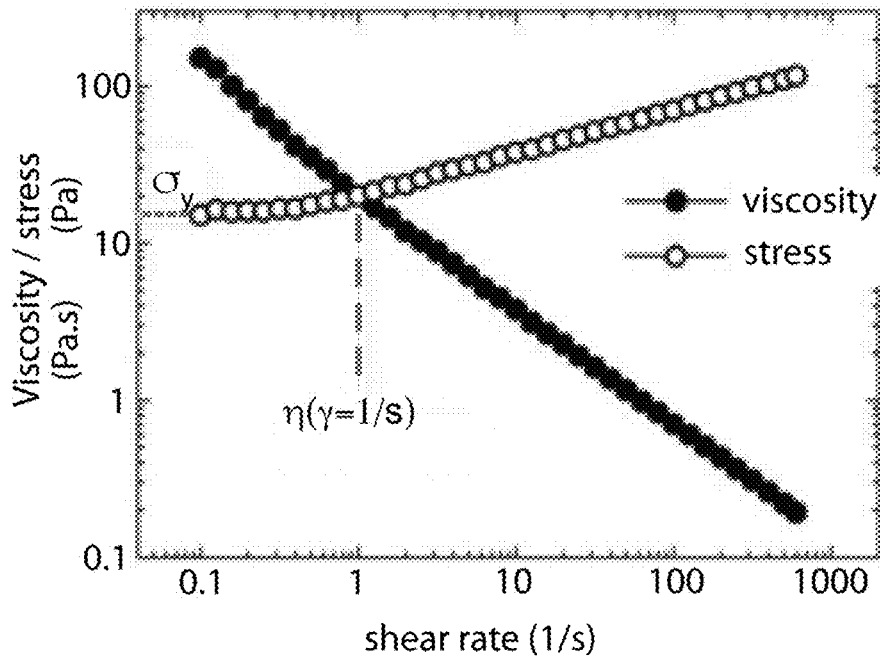
FIGS. 4A and 4B illustrate the rheological behaviour of a 1% by weight (w/v) solution of polysaccharide in water at 20° C. under different physical conditions, wherein (A) it is provided example data illustrating the dynamic viscosity (Pa·s) and stress (Pa) of the polysaccharide as a function of shear rate (1/s), enabling a calculation of yield stress ($\sigma_y$) and (B) it is provided example data for a typical plot of the measured zero shear viscosity of the polysaccharide as a function of applied stress, also allowing calculation of the yield stress ($\sigma_y$).
Figure 4B:
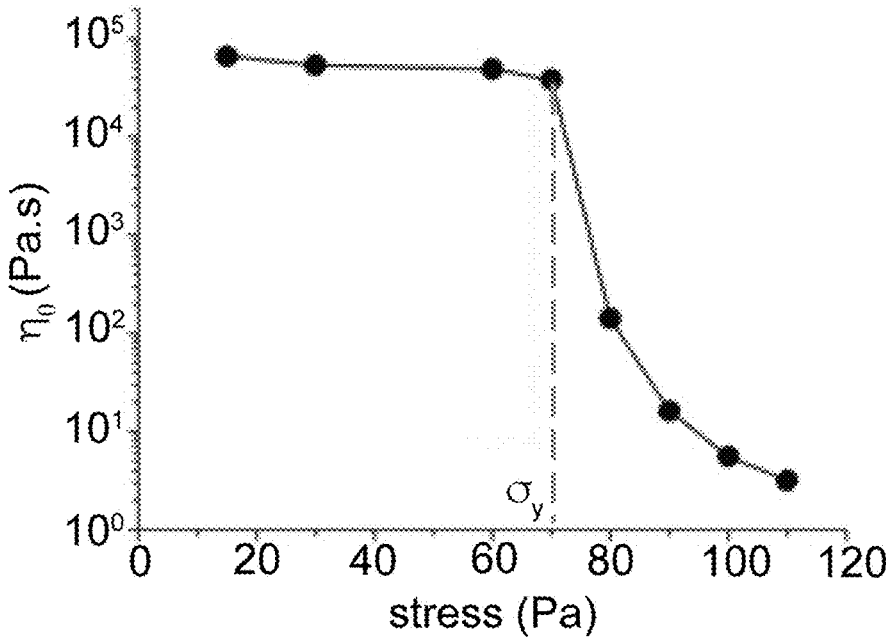
Figure 5:
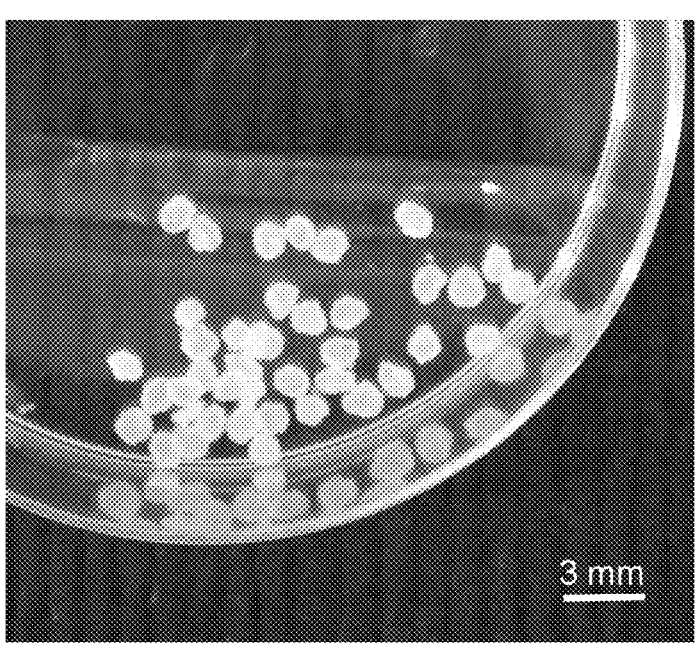
FIG. 5 illustrates the appearance of beads of polysaccharide, wherein it is provided that the beads are comprised by releasing microdrops of a polysaccharide solution into a solution of the polymer polyDADMAC (scale bar 3 mm).
Figure 6:
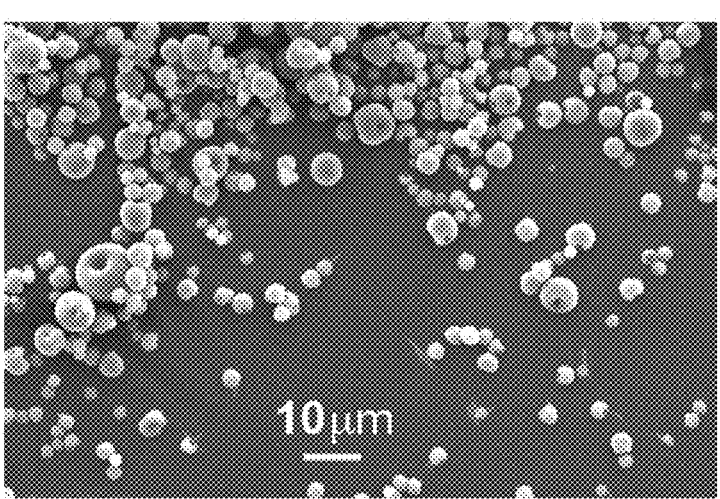
FIG. 6 illustrates a scanning electron microscope image of spray dried polysaccharide particles, wherein particles were formed using a GEA mobile pilot spray dryer unit (conditions inlet at 180 to 200° C., outlet at 80-100° C.; pump speed 25 to 40 ml/min), (bar=10 μm).

The polysaccharide discussed herein as also discussed in EP2846813B1 is characterised by at least one, at least two, at least three, at least four, or at least five of the characteristics (i), (ii), (iii), (iv), and (v).

(i) Molecular weight range (ii) Monosaccharide composition (iii) Immunomodulatory activity (iv) Sulphate content (as a percentage of molecular weight of the molecule)

(v) Viscosity/gel-forming properties.

As discussed, in EP2846813B1 in embodiments the polysaccharide of the present invention can comprise about 20 to 30% Glucose, 30 to 60% Galactose, 4 to 19% Arabinose, 2 to 6% Uronic acids, and a small percentage (1 to 10%) of other sugars, more particularly 1-4% Rhamnose, 1-3% Xylose, 1-10% Mannose (% by weight). In further embodiments, the polysaccharide can comprise about 25 to 29% Glucose, 35 to 47% Galactose, 14 to 15% Arabinose, 4 to 6% Uronic acids, and a small percentage (1 to 4%) of other sugars, more particularly 2.4% Rhamnose, 1.8% Xylose, 3.3% Mannose (% by weight).

The polysaccharide for use in the present invention preferably has a sulphate content of about 17 to 35% by weight and can demonstrate immunomodulatory activity in vitro, wherein for example the polysaccharide can inhibit neutrophil elastase activity by about 60 to 90%, in particular 60 to 80% relative to neutrophils to which the polysaccharide is not provided.

Fragments of the polysaccharide can comprise about 30 to 40% Glucose, 30 to 40% Galactose, 8 to 14% Arabinose, 7 to 11% Uronic acid and a small percentage (1 to 10%), suitably a small percentage (1 to 4%) of other sugar units (% by weight). Suitably fragments can comprise 35% Glucose, 35% Galactose, 11% Arabinose, 9% Uronic acid and a small percentage (1 to 10%), suitably a small percentage (1 to 4%) of other sugar units (% by weight).

Suitably a fragment of the polysaccharide can comprise about 8.4% Arabinose, 0.7% Rhamnose, 2.0% Xylose, 2.2% GalA (galacturonic acid), 57.9% Galactose, 24.6% Glucose, 3.8% GlcA (glucuronic acid) by weight. Suitably, a fragment of a polysaccharide may have a sulphate content of about 20 to 35% by weight, suitably 25 to 30% by weight.

Also described herein is a fragment of the polysaccharide which can demonstrate immunomodulatory activity in vitro by inhibition of IL6 and IL17C release from human keratinocytes by about 50-70% relative to human keratinocytes to which saccharide fragments is not provided. Also described herein is an fragment of the polysaccharide which can inhibit the release of interferon gamma from human peripheral blood mononuclear cells (PBMCs) by about 50-70% relative to human PBMC's in which fragment is not provided. In embodiments polysaccharide fragments can inhibit the chemotaxis of human neutrophils in vitro by about 50-70% and of THP-1 (monocyte) cells by about 30-50% relative to neutrophils and monocytes to which the oligosaccharide is not provided.

Routes of Administration

Suitably, the compositions and compositions use disclosed herein may be formulated tor administration by various routes.

The pharmaceutical compositions of this invention may be administered orally, parenterally, by inhalation spray, topically, rectally, nasally, buccally, vaginally or via an implanted reservoir, preferably by oral administration or administration by injection dependent on intended use. The pharmaceutical compositions of this invention may contain any conventional non-toxic pharmaceutically acceptable carriers, adjuvants or vehicles. In some cases, the pH of the formulation may be adjusted with pharmaceutically acceptable acids, bases or buffers to enhance the stability of the formulated polysaccharide or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Protection of Skin from Irritants

Without wishing to be bound by theory, polysaccharides of the present invention are considered to provide a protective effect to the skin from environmental irritants including chemical and particulate substances such as pollutants, as well as dry conditions, by exerting an anti-oxidant activity, and promotion of improved skin barrier function. Enhancement of skin barrier function may be by blocking adhesion of particulates to the skin, by for example forming a film on the skin, to provide a barrier against environmental irritants such as poly-halogenated aromatic compounds and heavy metals.

In embodiments of the invention, the polysaccharide or fragment of the polysaccharide from *P. capsulatus* disclosed in EP2846813B1 can be use in the reduction of skin irritation caused by, biological, chemical and environmental irritants, for example but not limited to, urban dust particles (such as PM 2.5 particles).

Suitably a composition comprising the polysaccharide or fragment thereof for topical use wherein the polysaccharide or fragments of the polysaccharide from *P. capsulatus* is provided in an amount between at 0.001 to 2% or 0.01 and 2%, advantageously between 0.1 and 1%, by weight (w/v) may be provided.

The average molecular weight of the polysaccharide is between 1000 and 40,0000 kDa, more particularly between 5,000 and 20,000 kDa and the average molecular weight of fragments of the polysaccharide will be between 5 and 1000 kDa, more particularly between 50 and 500 kDa. Fragments of the polysaccharide may provide the advantage of greater skin penetration. In embodiments other active agents, such as the anti-oxidants astaxanthin at between 0.005 and 0.1% by weight (w/v), or tocopherol acetate at between 0.1 and 2.5%, can be included in the composition. It is known that antioxidants may be useful to control inflammatory responses caused by oxidative stress, which is often a factor in skin irritation. The composition can be applied to skin daily, or preferably twice daily, in a gel or cream formulation, to reduce skin irritation. The composition provides advantages over the described state of the art by protecting the skin by both reducing the effects of irritation, and promoting skin function, such as improvement in the skin barrier.

Examples demonstrating the utility of a composition of the polysaccharide, or fragments of the polysaccharide, of the invention, to protect the skin from irritants is provided below as a model for irritants generally. Two different irritants were selected as examples of irritants—the detergent sodium lauryl sulphate, and a pollutant urban dust.

Example 1

Reduction of Sodium Lauryl Sulphate (SLS) Induced Erythema in Human Volunteers

The anti-irritant properties of chemical compounds can be tested using many different formats. Specifically, a single-blind within subject comparison study was conducted in 20 healthy male and female subjects to investigate the anti-irritant efficacy of the test article and an untreated site, following open-application. The test articles were formulated creams containing 1% by weight (w/v) of the polysaccharide or of said polysaccharide obtainable from the microalgae, *Prasinococcus capsulatus* and strains related to *P. capsulatus*, or the base cream without polysaccharide.

The control was applied on patches which consisted of 5 cm wide strips of occlusive Blenderm (3M Co) tape, to which Webril (Kendall Corporation) disks, approximately 2 cm square were fixed along the midline. Nine open-applications were applied, with assessments on study days 1, 2, 3, 4, 7, 8, 9, 10, 11 and 14. Individual erythema scores, mean scores and standard deviations for each study day were obtained for all 20 subjects.

The Positive Control (0.3% w/v SLS) elicited significant erythema throughout the study, as would be expected. Each test article reduced the erythema by day 14, resulting in no erythema being exhibited at the end of the study. The data from the Baseline measurements demonstrated that there were no statistically significant differences (P>0.05) between the test sites and the untreated sites prior to application of the test article. This confirmed the validity of the study.

After application, the test articles containing fragments of *P. capsulatus* polysaccharide, or no *P. capsulatus* polysaccharide produced statistically significant anti-inflammatory effects on the skin (P<0.05) when compared to the untreated site for all the time points up to and including the day 12 measurement. The test article containing *P. capsulatus* polysaccharide produced statistically significant anti-inflammatory effects on the skin (P<0.05) when compared to the untreated site between and including, the day 4 and day 12 timepoints.

The conclusion was that the test article containing *P. capsulatus* polysaccharide clearly showed the best efficacy, followed by the test article containing fragments of *P. capsulatus* polysaccharide, followed by the base cream. It was also concluded, that all of the test articles can be considered as safe for use under the conditions of the study and claims such as "Anti-inflammatory", "Skin soothing" and "Reduces redness" are all substantiated.

Example 2

Protection of Normal Human Keratinocytes Against Urban Dust

The anti-pollution properties of substances can be tested in various formats including cell based in vitro and human based in vivo approaches. Specifically, the protective effects of the polysaccharide or fragments of said polysaccharide obtainable from the microalgae, *Prasinococcus capsulatus* and strains related to *P. capsulatus*, against urban pollution were evaluated on normal human epidermal keratinocytes (NHEK) by measuring the viability of NHEK after intoxication with urban dust (Urban dust 1649b) pollution.

Cells (triplicate wells per treatment) were pre-incubated with the product (dose-response) for 24 hours, and then subjected to urban dust challenge (0.5 mg/ml) for a further 48 hours (n=3). After incubation, the culture supernatants were discarded and the NHEK viability was evaluated on the cell layers using a standard MTT reduction assay.

The results indicated that under the test conditions 0.3 mg/ml fragments of *P. capsulatus* saccharide exhibited a 56% increased protective effect on cells after exposure to urban dust, compared to the control (p=0.01 to 0.05). Other responses did not reach significance under these test conditions (*P. capsulatus* saccharide at 0.0001 mg/ml exhibited 20% protection). This effect is notable compared to other 'anti-pollution' cosmetic products. For example, 0.5% Pollushield™ was reported to have 47.9% protective effect on human epidermal keratinocytes (HEKa) treated with only 0.1 mg/ml urban dust (24 hours product pre-treatment, 24 hours urban dust incubation).

Wound Care

In embodiments of the invention, the polysaccharide and fragments of the polysaccharide from *P. capsulatus* disclosed in EP2846813B1 and also herein can be used in materials and compositions for the treatment and management of all types of wounds, to promote wound healing and reduce scarring.

Without wishing to be bound by theory, it is considered the polysaccharide and fragments thereof may absorb exudate, modulate wound hydration, be non-adherent, antimicrobial, strengthen new tissues, and reduce scarring. The preparation of a composition of the polysaccharide will allow for sterilisation once prepared, without compromising the formulation properties.

The biochemical structure of the polysaccharides provide suitable physical and biological characteristics that that allow for formulations which promote wound healing and control moisture. Materials suitable for use as a dressing in the care of wounds disclosed herein may also contain at least one other biological agent that promotes the natural healing process of wounds, such as silver sulphadiazine. In addition, the present invention provides methods of preparing such materials used as wound dressings.

*P. capsulatus* polysaccharide fibres for wound dressings may be prepared according to any method known in the art and include, for example, the methods described in Kong and Zeigler 2011 (*Fabrication of k-carrageenan fibres by wet spinning: spinning parameters*. Materials 4 (10): 1805-1817), or Wang et al. 2018. (*Preparation of carrageenan fibres with extraction of Chondrus via wet spinning process*. Carbohydrate Polymers 194: 217-224). The polysaccharide fibres used for the present invention are wet spun by continuous extrusion of an aqueous solution of the polysaccharide, which comprises between 0.01 and 2%, preferably between 0.5 and 1.5% by weight (w/v), and average molecular weight between 1,000 and 40,000 kDa, preferably between 10,000 and 20,000 kDa, into a bath of solvent, which comprises between 70 to 100% ethanol, methanol or acetone. Fibres can be woven into dressings, which can be applied to wounds for wound hydration management and promotion of healing. Silver sulfadiazine may also be incorporated into the dressing material at 0.05 to 0.25% by weight (w/v).

In addition, films may be prepared from *P. capsulatus* polysaccharide according to any method known in the art, for example, the wet casting technique described by Oun and Rhim 2017 (*Carrageenan-based hydrogels and films: Effect of ZnO and CuO nanoparticles on the physical, mechanical, and antimicrobial properties*. Food Hydrocolloids 67: 45-53). In the preferred invention the polysaccharide comprises between 0.01 and 2%, preferably between 0.5 and 1.5% by weight (w/v), and average molecular weight between 1,000 and 40,000 kDa, preferably between 10,000 and 20,000 kDa. It is mixed well with 'plasticising' agents such as glycerol at between 0.05 and 2%, preferably 0.25 and 1% by weight (w/v), heated to between 30 and 90° C., preferably between 40 and 70° C., cast into thin sheets of between 2 and 5 mm depth, and air dried, to form clear films suitable for wound dressing applications.

The films may also be solvent cast by immersion of the polysaccharide/glycerol composition in 70-100% ethanol, methanol or acetone. Dried films can be incorporated into dressings, which can be applied to wounds for wound hydration management and promotion of healing.

In embodiments, the present invention also relates to use of a polysaccharide, or fragments of polysaccharide obtainable from the microalgae, *Prasinococcus capsulatus* in a sterile gel composition for application to the surface of wounds, including burns. The present invention also relates to a method of sterilising such gel compositions.

Gel compositions comprising a polysaccharide or fragment thereof for application to the surface of wounds to assist healing may form a wound-friendly and humectant wound contact layer between the wound surface and conventional wound dressing layers. This helps to reduce the adherence of conventional wound dressings, such as bandages or gauzes, to the wound surface. The gel may also be formulated to provide other agents such as antimicrobials, or vitamins to promote healing.

The present invention provides an aqueous gel composition for use as a wound dressing comprised of polysaccharide or fragments of polysaccharides from *Prasinococcus capsulatus*, as described herein. In embodiments the gel compositions comprise between 0.01 and 2%, preferably 0.1 and 0.5% by weight (w/v) of the polysaccharide. The gel formulation may include other active materials such as between 0.01 and 10% by weight (w/v) antiseptics such as chlorhexidine, analgesics such as ibuprofen at between 1 and 5% by weight (w/v) and vitamins such as tocopherol acetate between 0.1 and 2.5% by weight (w/v).

In embodiments, compositions comprising *P. capsulatus* polysaccharide at an average molecular weight between 1,000 and 40,000 kDa, suitably between 10,000 and 20,000 kDa may be used.

These compositions have the added advantage over existing state of the art in that sterilisation can be carried out whilst still retaining suitable viscosity, allowing the gels to be coated onto the wound site in a convenient format, while retaining the healing properties of a natural polysaccharide. This is a consequence of the high molecular weight of the polysaccharide, which means that even after the fragmentation caused by selected sterilisation protocols, the polymer still retains viscosity. Sterilisation may be carried out by one of several methods. For example, this may be by irradiation up to 10 kGy. This allows the whole preparation to be packed prior to treatment, meaning dispensing and packing of the gel does not have to be carried out under sterile conditions.

Example 3

Enhancement of Expression of Epidermal Differentiation Markers and hBD-2 in Normal Human Keratinocytes The effects of substances on epidermal barrier formation can be tested in various formats including cell based in vitro and human based in vivo approaches. Specifically, the effects of fragments of the polysaccharide obtainable from the microalgae *Prasinococcus capsulatus*, and strains related to *P. capsulatus*, on gene expression in normal human epidermal keratinocytes (NHEK) in vitro was evaluated.

Cells were grown for 72 hours, prior to treatment with test saccharides, a reference material (cytokine mix; IL17, OSM and TNFa each at 3 ng/ml), or an untreated control. After a 24-hour incubation period with the test substance, the supernatant was removed and the cells were immediately frozen.

The analysis of gene expression was carried out (n=2), by extraction of RNA (quality controlled by Bioanalyzer 2100), reverse transcription and quantitative PCR, using GAPDH as the reference gene. GAPDH expression is constitutive and theoretically stable, so should not be impacted by the test articles. Relative expression of target genes was calculated compared to the untreated control.

The test saccharides showed no impact on housekeeping gene expression. Out of 16 gene profiles it was determined that polysaccharide fragments from *P. capsulatus* as discussed herein induced a strong concentration-dependent stimulation of the expression of only two genes: (i) KRT10 (keratin 10 epidermal differentiation marker) –0.03 mg/ml saccharide resulted in >1000% upregulation, and (ii) DEFB4A (anti-microbial peptide human beta-defensin 2) –0.03 mg/ml saccharide resulted in >600% upregulation.

The results suggested that test saccharides have pro-differentiating properties, which could promote epidermis formation and protection, and can modulate markers of innate immunity. These properties would both enhance barrier formation in normal skin and support the later stages of wound healing.

Anti-Fibrotic Effects

In embodiments of the invention, the polysaccharide and derivatives of the polysaccharide disclosed in EP2846813B1 and as discussed herein can be provided in topical compositions for the treatment and prevention of fibrotic conditions. In particular embodiments this includes the prevention of excess scarring, postoperative surgical adhesions, and conditions such as keloid trait, which share similar biology with fibrous adhesions.

The formation of scar tissue and fibrous adhesions is a major problem in post injury or post-operative recovery, or in association with the use of internal medical devices such as hernia meshes. It can result in significant discomfort, further illness or requirement for additional surgery. Keloid scarring is a hyper-proliferative, benign tumour-like skin condition characterised by recurrent and excessive scarring. It occurs frequently after burns and surgical procedures due to abnormal wound healing processes in the epidermal and dermal layers, and non-surgical treatment options are limited.

Without wishing to be bound by theory, it is considered the polysaccharides and fragments thereof can inhibit the cellular mediators of excessive fibrosis, such as transforming growth factor beta-1. Further, they can regulate several other drivers of fibrosis through their anti-inflammatory (for example reduction in IL8 production by keratinocytes) and anti-thrombotic (elevated activated partial thromboplastin time) effects.

Further, due to their physical characteristics including molecular weight, solubility and biocompatibility, gels or films provided by the polysaccharides and fragments thereof can prevent the formation of fibrotic adhesions, and remain in the treatment site until they are degraded.

In embodiments the composition may be used for the reduction and prevention of scarring of the skin, including in keloid trait and keloid scars, and in embodiments it may be used as a treatment to prevent post-operative adhesions and development of fibrous lesions. Compositions are formulated as gels, creams, films or sprays at Between 0.001% and 2%, between 0.02% and 2%, preferably between 0.1% and 0.5% by weight (w/v) of polysaccharide. In embodiments the polysaccharide has an average molecular weight between 1000 and 40,000 kDa, more preferably between 5,000 and 20,000 kDa, and fragments of the polysaccharide have an 15 average molecular weight between 5 and 1000 kDa, preferably between 20 and 500 kDa, more preferably between 50 and 200 kDa.

The high molecular weight polysaccharide can also be delivered as a natural gel, or spray, without the need for other humectants, which can help it to be retained in the effected areas for longer and can form a barrier in the case of fibrous adhesions.

Anti-Viral Effects

In embodiments of the invention, the polysaccharide and derivatives of the polysaccharide disclosed in EP2846813B1 can be for use in anti-viral therapy and prophylaxis including for nasal and other topical applications.

It is considered that certain sulphated polysaccharides will demonstrate anti-viral activity against a wide range of viral strains. In particular, it is considered they may be effective against various enveloped viruses and in particular against herpes simplex virus (HSV), Papilloma viruses and HIV.

Suitably, compositions comprising the polysaccharide or fragments thereof may be applied topically on skin and/or mucosal surfaces to reduce or prevent infection of viral strains including, but not limited to, HSV-1 and 2, HIV, HPV, influenza viruses, respiratory syncytial virus, rhinoviruses, adenoviruses, papovaviruses, retroviruses, flaviviruses, hepadnaviruses, poxviruses and coronaviruses. Suitably, the viruses include, but not limited to. HSV-1 and 2, HIV, HPV, influenza viruses, rhinoviruses, and coronaviruses such as Sars CoV-2. Compositions are formulated as gels or creams at between 0.0001% and 2%, between 0.02% and 2%, preferably between 0.1% and 0.2% by weight (w/v) polysaccharide or fragments of polysaccharide. The polysaccharide has an average molecular weight between 1000 and 40,000 kDa, and the fragments of the polysaccharide have an average molecular weight between 5 and 1000 kDa.

Viral infections of the respiratory tract are caused by more than 150 different viruses including human rhinoviruses, parainfluenza virus (1-4), metapneumovirus, respiratory syncytial viruses, influenza (A, B, C), and more. Allergic reactions in the nasal cavity may be due to a temporary allergy such as against certain pollen, or specific triggers to which the subject has sensitivity, such as dust mite antigens. A key symptom in respiratory viral infection and allergy is a blocked and runny nose. It is known in the art that respiratory viral infections can exacerbate existing allergic disease. For example, if patients, who suffer temporary allergic responses such as to pollen, suffer recurrent respiratory viral infections, then this increases their risk of developing allergic asthma.

The present invention provides that the polysaccharide and derivatives of the polysaccharide from *P. capsulatus* disclosed in EP2846813B1, can be used in the treatment of respiratory viral infection and nasal congestion due to allergy, by way of a specific formulation in a nasal spray delivery format. Hyperosmolar ionic conditions normally used to reduce nasal congestion can effect polysaccharide conformation, and reduce their effectiveness, by reducing viscosity and therefore retention on the mucosal surfaces. The biochemical structure of the polysaccharides provide suitable physical and biological characteristics that enable prophylactic treatment of nasal viral infection, and allow for formulations which support decongestion. It is therefore considered that the sulphated polysaccharides of the present invention will combine both an anti-viral and a rapid decongestant effect when delivered in nasal spray formulation.

*P. capsulatus* polysaccharides can be formulated into a novel pharmaceutical composition to combine the antiviral efficacy with a decongestant activity, where decongestant relates to activity which leads to partial or complete unblocking of the nose due to, for example, allergy or viral infection. This goal is achieved by providing the polysaccharide and fragments thereof which retain suitable viscosity. In preferred embodiments fragments of the polysaccharide have an average molecular weight between 5 and 1000 kDa, preferably between 20 and 500 kDa, more preferably between 50 and 200 kDa. In preferred embodiments the polysaccharide has an average molecular weight between 1000, suitably 2000 and 40,000 kDa, more preferably between 5,000 and 20,000 kDa. The formulation will be balanced to provide a hyper-osmolar condition suitable to promote nasal decongestion. The formulation will comprise between 0.0001% and 2%, between 0.02% and 2%, preferably between 0.1% and 1% by weight (w/v) of polysaccharide for anti-viral efficacy. It will be rendered sufficiently hyper-osmolar by use of sodium chloride solution, or other alkali metal salt, at concentrations between 0.1% and 3% by weight (w/v), combined with a short-chain sugar selected from the group of mono-, di-, and oligosaccharides, and/or together with a polyol such as sorbitol at concentration between 1% and 15% by weight (w/v), in a suitable combination to retain polysaccharide activity. The spray will b e administered directly into the nose to reduce and prevent viral infection, and to promote nasal decongestion.

Example 4

Anti-Viral Properties of Saccharides from *P. capsulatus*

The anti-viral properties of a substance may be determined by a number of different methods. Specifically, the anti-viral effects of the polysaccharide and fragments of the polysaccharide obtained from *Prasinococcus capsulatus*, were evaluated using in vitro cell-based infectivity assays with Respiratory syncytial virus (RSV), Herpes simplex virus1 (HSV1), Rhinovirus/EV-D68, and influenza virus H1N1.

Five saccharides were tested for their anti-viral effects: i) high molecular weight (HMW) polysaccharide which had been filter sterilised, ii) HMW polysaccharide which had been briefly autoclaved, iii) a saccharide fragment with estimated average MW of 35 kDa (depolymerised saccharide 1), iv) a saccharide fragment with estimated average MW of 35 kDa which had been further purified by ion-exchange chromatography (depolymerised saccharide 2) and v) a saccharide fragment with estimated average MW of 47 kDa (depolymerised saccharide 3).

For RSV, HSV-1 and Rhinovirus/EV-D68 anti-viral assays test saccharides were first tested for cytotoxic effects on the virus host cell lines Hep2 (ATCC CCL-23) and MRCS (ATCC CCL-171). Cells were plated at 8000 per well in a 96-well plate, in complete DMEM (Sigma Aldrich). 24 hours after seeding cells were incubated with test saccharides at 8 different concentrations in media, in duplicate. Cells were then incubated at 37° C. and 5% $CO_2$ for 4 days. Cells were stained for 30 minutes at 37° C. with Image-iT Dead Green Viability Stain (Invitrogen), which is impermeant to healthy cells, and with MitoTracker Orange (Invitrogen), which stains active mitochondria. Cells were then fixed in formalin, washed, and stain with PBS Hoechst nuclear stain. Data was acquired by a Thermo Cell Insight CX7 HCS microscope using a compartmental analysis algorithm. Gemcitabine was used as a positive control to verify the performance of the staining.

The test saccharides were found to have no cytotoxic effects on the host cells at all the concentrations tested (CC50 was above 0.5 mg/ml in all cases), with no negative effects on cytoplasmic membrane permeability or mitochondrial signal.

To determine the anti-viral effect of test saccharides on RSV (strain long), HSV1 (strain 17+), and Rhinovirus (EV-D68), Hep2 or MRCS cells were plated at 8000 per well in complete DMEM. 24 hours after seeding cells were incubated with test saccharides at 6 different concentration in triplicate and with RSV at 0.5 multiplicity of infection (MOI) or HSV at 0.0007 MOI. In the case of EV-D68, 24 hours after seeding, MRCS cells are incubated for 2 hours with test saccharides at 8 concentrations and EV-D68 at MOI 0.1 at 33° C. The supernatant is then removed and cells are treated with test saccharides at 8 concentrations.

24 hours to 4 days post infection cells were fixed and stained with anti-RSV antibody (ab20745) or anti-HSV1 ICP8 antibody (ab20194) or anti-dsRNA (Scions J2) for EV-D68, and PBS Hoechst. Plates were imaged by a Thermo Cell Insight CX7 HCS microscope using a compartmental analysis coupled with a spot detector algorithm to detect and quantify the infection rate (number of fluorescent cells over number of total cells). Results were calculated based on automatic measurement of at least 2000 cells (MRCS) or 6000 cells (Hep2) per replicate. Data was normalised to an untreated control. Acyclovir was used as a positive control of HSV anti-viral activity.

The results indicated that the polysaccharide and fragments of the polysaccharide obtained from *Prasinococcus capsulatus* have antiviral effects against HSV1, RSV and Rhinovirus/EVD68 under the described conditions. Antiviral effects of fragments of the polysaccharides on RSV and HSV demonstrated high potency and selectivity.

To determine the anti-viral effects of fragments of the polysaccharide obtained from *Prasinococcus capsulatus* on influenza virus (strain Influenza A (H1N1) A/Brisbane/59/ 2007) an accelerated viral inhibition assay (AVINA) was carried out, with cytotoxicity testing performed in parallel. A549 cells were plated in DMEM and 1% penicillin/streptomycin and incubated overnight at 37° C./5% CO2. One 96-well plate was set up for anti-viral testing, and another for cytotoxicity testing. Test saccharides were added to the assay plates at 10 concentrations, followed by addition of diluted H1N1 virus to the viral assay plate at 0.1 MOI, or media in the case of the cytotoxicity plate. Plates were incubated for 72 hours at 37° C./5% CO2. Viral infection was determined by measuring neuraminidase activity by the addition of 4-methylumbelliferyl N-acetyl-a-D-neuraminic acid sodium salt substrate (MU-NANA) and measurement of the resulting fluorescent signal. Cytotoxicity was evaluated by addition of ViralToxGlo (Promega) substrate to the cultures, resulting in a luminescent signal correlating to cellular ATP activity.

The test saccharides were found to have no cytotoxic effects on the host cells within the concentration range tested. Anti-viral testing results demonstrated that fragments of the polysaccharide obtained from *Prasinococcus capsulatus* reduce the influenza neuraminidase signal in a dose dependent manner, with maximum viral inhibition of 60-70% under the described conditions.

Lubricants

In embodiments of the invention, the polysaccharide and fragments of the polysaccharide from *P. capsulatus* disclosed in EP2846813B1 and as discussed herein can be used as medical bio-lubricants for epithelial tissue layers, especially mucosal tissue.

Natural polysaccharides have diverse functions and biological properties and are increasingly exploited for their rheology and tribological properties, including as water-based bio-lubricants. The use of these charged natural polymers provides superior functionality over other lubricants, due to their physiochemical characteristics, molecular weight, controlled degradation and biocompatibility. The most commonly described is the use of hyaluronic acid as a joint and eye lubricant, but the state of the art also encompasses other saccharides such as chitosan, carrageenan and those derived from the microalgae *Porphyridium* sp (Gourdon, D. et al. 2008. *Adhesion and Stable Low Friction Provided by a Subnanometer-Thick Monolayer of a Natural Polysaccharide*. Langmuir 24: 1534-1540; Eguiluz, R. et al. Lubrication and Adhesion by Charged Biopolymers for Biomedical Applications. In Biopolymers, Magdy Elnashar (Ed.), InTech, pp 257-270).

It is considered the polysaccharide may function by holding water at the epithelial surface. Further, the polysaccharide has suitable sheer thinning and viscosity properties to provide lubrication to the surface.

The composition is a naturally derived viscoelastic gel having a suitable viscosity, pH, high molecular weight, and sheer-thinning properties. Suitably, sheer-thinning properties may be provided when the composition comprises between 0.01% and 2%, between 0.02% and 2%, suitably between 0.1% and 1% by weight (w/v) of polysaccharide, with an average molecular weight of between 1000 and 40,000 kDa, more preferably between 5,000 and 20,000 kDa. The composition may be formulated with the addition of polyols, such as glycerol, or propylene glycol, which act together with the polysaccharide to slow evaporation and 'plasticise' the surface.

These polyols may be incorporated at between 1% to 15% of the system, or more preferable 5% to 10% by weight (w/v). The invention provides particular advantages over existing state of the art due to its high average molecular weight, and high viscosity at lower concentrations.

The lubricant may be used for intra-vaginal lubrication, or as a lubricant for medical instruments. Another aspect of the invention may be as a contact fluid for ultrasonic investigations or treatment, to aid contact and movement over the skin.

Example 5

Rheological Properties for Lubricants

The lubricant effects of substances can be determined using various approaches to determine key rheological, tribological and performance characteristics. Specifically, the lubricant potential of polysaccharide obtainable from the microalgae, *Prasinococcus capsulatus* was determined by measuring its rheological properties. A sample of polysaccharide was freeze-dried and dissolved at 1% by weight (w/v) in the appropriate quantity of stock solution. Samples were vortex mixed and then refrigerated for 3 days to 1 week before measurements were carried out at room temperature.

Measurements were carried out between crosshatched steel surfaces employing a plate-plate geometry on an AR2000 rheometer from TA Instruments. The diameter of the upper plate was 4 cm and plate separation was 100 µm. Temperature was controlled through a Peltier Plate within the stage, and measurements were carried out at 20° C. Rough surfaces, were required to prevent slip occurring at the metal surface. A solvent trap was used to prevent evaporation from the sample during the course of measurements.

Creep measurements were carried out to establish the yield stress of the polysaccharide. Measurements were repeated at increasing levels of applied stress. Each level of stress was applied for 10 minutes, and the sample was allowed to relax for two minutes, before another level of stress was applied. For flow measurements the upper surface is rotated at a velocity that will achieve the desired shear rate while the stress that must be applied in order to achieve this velocity is measured. Measurements were carried out by applying a fixed shear rate to the polysaccharide sample and measuring the viscosity and shear stress when the sample reached a steady state (or had completed three cycles). Measurements were carried out between shear rates of 0.01 s$^{-1}$ and 600 s$^{-1}$. The yield stress was extracted from the lowest level where stress was independent of the shear rate (usually consistent with the intercept on the y-axis).

Although samples appear homogeneously dispersed after a few hours, tests were also carried out over time, to examine any changes to the yield stress, zero shear viscosity and viscosity, all measured at a shear rate, $\gamma=1/s$. The measured values of the yield stress, ay, measured through creep (cr) and flow (fl) measurements, as a function of the time elapsed since sample preparation, are presented in the table below. In addition, the zero shear viscosity measured through creep measurements and viscosity at a shear rate, $\gamma=1/s$, are presented.

| Elapsed time | $\sigma y$ (Pa) (cr) | $\sigma y$ (Pa) (fl) | $\eta_0$ ($\times 10^4$) Pa · s | $\eta$ (y = 1/s) Pa · s |
|---|---|---|---|---|
| ¼ day | 70 | 41 | 5.3 | 60 |
| 2 days | n/a | 38 | n/a | 38 |
| 3 days | n/a | 43 | n/a | 50 |
| 7 days | 30 | 37 | 5.3 | 45 |
| Av. ± st. dev | 50 ± 28 | 40 ± 3 | 5.3 ± ± 0 | 48 ± 9 |

The results indicated that there was no systematic dependence on storage time up to 1 week and that the yield stress obtained through flow measurements provides results with a relatively small standard deviation, $\sigma_y=40\pm3$ Pa. There was little difference in the yield stress measured through creep and flow measurements. Since the material had a significant yield stress, this had to be overcome for the material to be sheared. The zero shear viscosity measured through creep measurements was high, $\eta_0\sim5.3\times10^4$ Pa·s, and reduced significantly and was rate dependent, reducing to $\eta=48\pm9$ Pa·s at a shear rate, $\gamma=1/s$.

It was determined that in deionised and distilled water the samples form viscoelastic gels with shear-thinning properties, suitable for bio-lubricant applications.

Flow measurements were also carried out for 1% by weight (w/v) polysaccharide solutions in distilled deionised water as a function of temperature, taking measurements at 20, 40, 50, 60 and 70° C. The results indicated that both the viscosity and the yield stress steadily decrease as the temperature increases, up 60° C., indicating no major change in stability at body temperature. Spray-drying induces large variations in the properties of the reconstituted gel due to change in conformation induced by the drying process. Encapsulation and Tissue Engineering In several embodiments of the invention, the polysaccharide and derivatives of the polysaccharide from *P. capsulatus* disclosed in EP2846813B1 and discussed herein can be incorporated into carrier devices, such as particles, hydrogels or scaffolds. In embodiments these devices enable the protection, delivery and controlled release of molecules, such as pharmaceuticals, enzymes, and fragrances. In other embodiments they provide the growth support, and delivery of cells, such as stem cells, for cytotherapy.

The state of the art provides the use of many different carrier devices for biological applications including those for drug delivery, tissue engineering and regenerative medicine. These carriers may be in the form of particles, capsules, hydrogels and scaffolds, used for delivery and release of cells, such as stem cells for regenerative medicine, and substances, such as antibodies. The use of carrier devices can result in improved efficacy of therapeutic treatments, by protection of reactive or unstable components until their release, and by sustained release in a specific location. In the case of supports for cells and tissues, growth can be enhanced by the 3D nature of the carrier and reactive chemical groups on its surface.

The polysaccharides of the invention are considered to have suitable properties for incorporation into biological carriers such as particles, capsules, hydrogels and scaffolds. These properties include high molecular weight, stability, solubility, and suitability for cross-linking. A carrier device may be produced by various techniques including 3D printing of the polysaccharide composition into scaffolds, or formation of particles and capsules from the polysaccharide by ionic gelation, covalent cross-linking, emulsions or polyelectrolyte complexing. It has been surprisingly found that the unusually high molecular weight and charge density of polysaccharides from *P. capsulatus* make it highly suitable for use in forming a carrier device, such as a particle, capsule, hydrogen or scaffold.

In particular, the polysaccharide can be used to make a carrier device comprising microbeads suitable for incorporation of molecules and cells, by any method described in the state of the art for example such as those disclosed in Venkatesan J. et al. 2016. (*Seaweed Polysaccharide-Based Nanoparticles: Preparation and Applications for Drug Delivery.* Polymers 8 (30)).

Suitably a method for the manufacture of porous microbeads from the polysaccharide may be by polyelectrolyte complexing. The polysaccharide component will comprise between 0.01% and 2%, between 0.1% and 2%, preferably between 0.5% and 1.5% by weight (w/v) and have an average molecular weight between 2000 and 40,000 kDa, more preferably between 10,000 and 40,000 kDa. It is combined with a solution of the cationic polymer poly (diallyldimethylammonium chloride) (polyDADMAC) at between 1% to 20%, preferably 2% to 10%, using polyDADMAC of molecular weight 1 to 500 kDa, preferably 50 to 200 kDa, using a fine nozzle, to allow bead formation. Molecular weight, speed, stirring time and temperature can be controlled, to manipulate bead formation and resulting characteristics such as size and strength.

The microbeads have superior stability, biocompatibility and solubility, allowing long-term storage, and they have been recovered intact after freezing at −20° C. for 7 days.

Example 6

Preparation of Polysaccharide for Encapsulation Techniques

The ability of the polysaccharide obtainable from the microalgae, *Prasinococcus capsulatus* to form structures, which could be used for encapsulation technologies was evaluated using a charged based approach. 10 mls of a 10 mg/ml solution of *Prasinococcus capsulatus* polysaccharide (non-sterile) was made up in water and stirred hard for 10 minutes to ensure polymer was dissolved, and then left standing to allow air bubbles to be released.

A polyDADMAC solution used was a 35% solution of <100 kDa polymer (SIGMA). It was diluted in mQ water to give a 4% solution (3 mls of polyDADMAC+23.25 mls of water). Drops (25 μl) of 10 mg/ml polysaccharide were dripped into the 4% polyDADMAC solution using a 200 μl pipette. The resulting beads were left for 30 minutes to fully react. Discrete beads were formed which were soft and rubbery to touch.

The process was repeated under saline conditions. 5 mg/ml and 2.5 mg/ml solutions of polysaccharide were prepared by 1:1 dilutions, to generate a series of solutions (10, 5, 2.5 mg/ml) in either water or 0.9% sodium chloride.

The polyDADMAC solution used was a 35% solution of <100 kDa polymer (SIGMA), prepared as described above. A second polyDADMAC solution was also prepared in exactly the same way, but it was diluted in 0.9% sodium chloride rather than water.

Approximately 500 µl of each polysaccharide solution was loaded into a 2 ml syringe. Small beads of each solution were dripped into the appropriate 4% polyDADMAC solution (ie. with or without sodium chloride) using a 25G needle. Beads were left for 10 minutes to fully react and then washed with water or saline.

The droplets of 10 mg/ml EPS formed discrete beads in the polyDADMAC solution whether solubilised in water or 0.9% NaCl. *P. capsulatus* polysaccharide solutions ≥5 mg/ml can form beads in polyDADMAC solutions, whether in water or sodium chloride. Bead strength and structure was not evaluated.

Beads were stored at 4° C. in solution for 4 years without signs of decomposition.

Although the invention has been particularly shown and described with reference to particular examples, it will be understood by those skilled in the art that various changes in the form and details may be made therein without departing from the scope of the present invention.

The invention claimed is:

1. A method of treating viral infection, the method comprising:

administering to a subject in need thereof a composition comprising a polysaccharide having an average molecular weight of between 1,000 and 40,000 kDa, or fragment thereof having an average molecular weight between 5 and less than 1000 kDa, wherein the polysaccharide is a sulphated heteropolymer obtainable from the order of Prasinococcales, and the polysaccharide or fragment thereof has a sulphate content of 17 to 35% by weight.

2. The method of claim 1, wherein the polysaccharide or fragment thereof comprises, by weight, about:

20 to 30% Glucose;
30 to 60% Galactose;
4 to 19% Arabinose;
2 to 6% Uronic acids; and
1 to 10% of other sugar units.

3. The method of claim 2 wherein the other sugar units comprise at least one of:

rhamnose;
xylose; and
mannose.

4. The method of claim 1, wherein the polysaccharide or fragment thereof has a sulphate content of about 20 to 30% by weight.

5. The method of claim 1, wherein the average molecular weight of the polysaccharide is between 5,000 and 20,000 kDa, or the average molecular weight of the fragment is between 20 and 500 kDa.

6. The method of claim 1, wherein the polysaccharide constitutes greater than 80% (by mass) of a dried product.

7. The method of claim 1, wherein the composition further comprises an aqueous solution;

and the composition is delivered to the skin, nasal, vaginal, or rectal surface by topical application.

8. The method of claim 7, wherein the polysaccharide or fragment thereof is provided in an amount between 0.001% and 2% by weight (w/v) of the composition.

9. The method of claim 1, wherein the composition is a gel, cream, or ointment.

10. The method of claim 7, wherein the composition further comprises at least one anti-oxidant.

11. The method of claim 7, wherein the composition further comprises an antiseptic.

12. A method for preparing a wound dressing material, wherein the wound dressing material comprises films of a polysaccharide; and the method comprises the steps of:

preparing an aqueous solution of between 0.01 and 2% by weight (w/v) of the polysaccharide having an average molecular weight between 1,000 and 40,000 kDa or fragment thereof;

mixing the aqueous solution with a plasticizing agent;

heating the mixture to a temperature of between 30° C. and 90° C.;

casting the solution to a thin sheet, optionally of between 2 and 5 mm, by wet or solvent casting; and drying the thin sheets to form the polysaccharide films; wherein the polysaccharide having an average molecular weight of between 1,000 and 10 40,000 kDa;

the polysaccharide fragment having an average molecular weight between 5 and less than 1000 kDa;

the polysaccharide is a sulphated heteropolymer obtainable from the order of Prasinococcales; and the polysaccharide or fragment thereof has a sulphate content of 17 to 35% by weight.

13. The method of claim 12, wherein the plasticizing agent is a polyol solution.

14. A wound dressing material, comprising a polysaccharide having an average molecular weight of between 1,000 and 40,000 kDa, or a fragment thereof having an average molecular weight between 5 and less than 1000 kDa.

wherein the polysaccharide is a sulphated heteropolymer obtainable from the order of 30 Prasinococcales, and the polysaccharide or fragment thereof has a sulphate content of 17 to 35% by weight; and the wound dressing further comprising a silver sulfadiazine in an amount between 0.05 and 0.25% by weight (w/v).

15. A method of preparing a carrier device, comprising incorporating a polysaccharide or fragment thereof into a carrier device wherein the polysaccharide has an average molecular weight of between 1,000 and 40,000 kDa and the fragment thereof having an average molecular weight between 5 and less than 1000 kDa; 30;

the polysaccharide is a sulphated heteropolymer obtained from the order of Prasinococcales; and the polysaccharide or fragment thereof has a sulphate content of 17 to 35% by weight.

16. The method of claim 15, wherein the method comprises complexing a solution of the polysaccharide with another polyelectrolyte to form a microparticle.

17. The method of claim 16, comprising the steps of:

providing the polysaccharide solution between 0.1 to 2% by weight (w/v); and extruding the polysaccharide solution from a tip of a capillary tube, or narrow gauge needle, into a solution of poly (diallyldimethylammonium chloride) between 1 and 20% by weight, and having a molecular weight between 1 and 500 kDa.

18. The method of claim 15, wherein the carrier device comprises a microparticle and the method further comprising a step of encapsulating an active pharmaceutical ingredient into the microparticle by pre-mixing with the polysaccharide solution.

19. The method of claim 15, wherein the carrier device comprises encapsulation of the active ingredient into microparticles by pre-mixing with the polysaccharide solution and spray drying.

20. The method of claim 15, wherein the carrier device comprises a microparticle and the method further comprising encapsulating a mammalian or bacterial cell into the microparticle by pre-mixing with the polysaccharide solution.

\* \* \* \* \*